United States Patent [19]

Lipsky et al.

[11] Patent Number: 5,346,888
[45] Date of Patent: Sep. 13, 1994

[54] DIPEPTIDE ALKYL ESTERS AND THEIR USES

[75] Inventors: Peter E. Lipsky, Dallas; Dwain L. Thiele, Coppell, both of Tex.

[73] Assignee: Board of Regents, The University of Texas System, Austin, Tex.

[21] Appl. No.: 994,600

[22] Filed: Dec. 21, 1992

Related U.S. Application Data

[60] Continuation of Ser. No. 643,580, Mar. 14, 1991, abandoned, which is a continuation-in-part of Ser. No. 168,177, Aug. 15, 1988, Pat. No. 5,047,401, which is a division of Ser. No. 774,051, Sep. 9, 1985, Pat. No. 4,752,602.

[51] Int. Cl.$^5$ ................... A61K 37/02; C07K 5/06
[52] U.S. Cl. ........................................ 514/19
[58] Field of Search ................................. 514/19

[56] References Cited

U.S. PATENT DOCUMENTS

| | | | |
|---|---|---|---|
| 4,555,502 | 11/1985 | Patchett et al. | 514/19 |
| 4,585,757 | 4/1986 | Pang et al. | 514/19 |
| 4,616,012 | 10/1986 | Neustadt et al. | 514/19 |

Primary Examiner—Lester L. Lee
Attorney, Agent, or Firm—Arnold, White & Durkee

[57] ABSTRACT

An alkyl ester of dipeptide comprising natural or synthetic L-amino acids with hydrophobic side chains is provided herein. Preferable amino acids are leucine, phenylalanine valine, isoleucine, alanine, proline, glycine or aspartic acid beta methyl ester. Preferable dipeptides are L-leucyl L-leucine, L-leucyl L-phenylalanine, L-valyl L-phenylalanine, L-leucyl L-isoleucine, L-phenylalanyl L-phenylalanine, L-valyl L-leucine, L-leucyl L-alanine, L-valyl L-valine, L-phenylalanyl L leucine, L prolyl L-leucine, L-leucyl L-valine, L-phenylalanyl L-valine, L glycyl L-leucine, L-leucyl L-glycine or L-aspartyl beta methyl ester L-phenylalanine. Most preferable dipeptides are L-leucyl L-leucine, L-leucyl L-phenylalanine, L-valyl L-phenylalanine, L-phenylalanyl L-leucine, L-leucyl L-isoleucine L-phenylalanyl L-phenylalanine and L-valyl L-leucine. The alkyl ester of the dipeptide is most preferably a methyl ester and may also be an ethyl ester or alkyl of up to about four carbon atoms such as propyl, isopropyl, butyl or isobutyl. These alkyl esters of dipeptides comprising amino acids with hydrophobic side chains may be used to deplete cytotoxic T-lymphocytes or natural killer cells from organisms, cell populations or tissues. The O-alkyl esters of the described alkyl dipeptide esters inhibit lethal graft-vs-host disease and allograft rejection, particularly skin allograft rejection by a transplant recipient. The dipeptide most preferably employed is the O-alkyl dipeptide ester, or Leu-Leu-OMe.

4 Claims, 9 Drawing Sheets

DIPEPTIDE ALKYL ESTERS AND THEIR USES

This application is a continuation of application Ser. No. 07/643,580, filed Mar. 14, 1991, and now abandoned, which in turn is a continuation-in-part of a divisional application U.S. Ser. No. 07/168,177, filed Aug. 15, 1988, and now U.S. Pat. No. 5,047,401. U.S. Ser. No. 07/168,177 is a divisional application of U.S. Ser. No. 774,051, filed Sep. 9, 1985and now U.S. Pat. No. 4,752,602. The parent application U.S. Ser. No. 774,051, filed Sep. 9, 1985, entitled, "Dipeptide Alkyl Esters and Their Uses" of the referenced divisional application, U.S. Ser. No. 07/168,177, has now issued as U.S. Pat. No. 4,752,602, dated Jun. 21, 1988. A continuous chain of copendency has therefore been maintained with the present application. Research involved in the development of the invention was supported by National Institutes of Health Grant AI-24639.

BACKGROUND OF THE INVENTION

L-leucine methyl ester (Leu-OMe) has previously been used as a lysosomotropic agent.[1-2] The generally accepted lysosomotropic mechanism involved leu-OMe diffusion into cells and into lysosomes, followed by intralysosomal hydrolysis to leucine and methanol. The more highly ionically charged leucine, largely unable to diffuse out of the lysosome, caused osmotic lysosomal swelling and rupture. The fate of leu-OMe subjected to rat liver lysosomes was additionally suggested by Goldman et al.[2] to involve a transpeptidation reaction and a resultant species-presumably the dipeptide which was further hydrolyzed to free amino acids. A subsequent and related paper by Goldman[3] postulates that non-methylated dipeptides are formed by lysosomes.

L-amino acid methyl esters have been specifically shown to cause rat liver lysosomal amino acid increases.[4] Leucine methyl ester has been shown to cause rat heart lysosomal swelling and loss of integrity.[5] absence of any known sensitization. This cytotoxic activity can be modulated by a host of pharmacologic agents that appear to act directly on NK effector cells. NK activity has been shown to be augmented after exposure to interferons,[6] interleukin 2,[6,7] and interleukin 1,[7] whereas target cell binding is inhibited by cytochalasin B,[8] dimethyl sulfoxide, 2-mercaptoethanol, and magnesium deficiency.[9] Subsequent steps in the lytic process are inhibited by calcium deficiency,[9,10] lysosomotropic agents,[11] prostaglandin E$_2$ PGE2,[12,13] cyclic AMP,[12,14] lipomodulin,[15] and by antagonists of lipoxygenase.[16] Furthermore, it has been demonstrated that PGE$_2$ and reactive metabolites of oxygen produced by monocytes (MP) or polymorphonuclear leukocytes (PMN) can inhibit NK cell function.[17-18]

Previous work by the present applicants has examined the effect of L-leucine methyl ester on the structure and function of human peripheral blood mononuclear cells (PBM).[1]

Human peripheral blood mononuclear cells (PBM) are capable of mediating a variety of cell-mediated cytotoxic functions. In the absence of any known sensitization, spontaneous lysis of tumor cells and virally-infected cells is mediated by natural killer cells (NK) contained within the large granular lymphocyte fraction of human PBM.[19] After lymphokine activation, additional cytotoxic lymphocytes capable of lysing a broad spectrum of tumor cell targets can be generated in in vitro cultures.[20,21] Furthermore, lymphokine activated peripheral blood mononuclear phagocytes (MP) are also capable of lysing certain tumor targets[22].

Cytotoxic lymphocytes, specifically cytotoxic T lymphocytes (CTL) have been shown to play a crucial role in solid organ allograft rejection.[7] The appearance of donor anti-host CTL is often associated with acute rejection of human renal allografts (Sabiston, 1986, in Textbook of *Surgery*, p. 418). Both natural killer (NK) cells and CTL are involved in rejection of bone marrow grafts[70]. Drugs such as cyclosporin A which prevent activation of CTL[71] have been described as effective in preventing organ allograft rejection (Sabiston, 1986, in Textbook of Surgery, p 415–416). Once CTL are activated, they are reported to be resistant to cyclosporin A[72]. It is therefore of interest that whereas cyclosporin A is a good prophylactic agent in preventing organ allograft rejection, once acute cellular rejection is initiated, cyclosporin A is not one of the agents effective in reversing ongoing rejection episodes (Sabistson at p. 441, 443–445, 447–448).

This reportedly relative inability of cyclosporin to "turn off" ongoing allograft rejection episodes is postulated to relate to cyclosporin A's lack of inhibitory effect on CTL. From the above observations, a significant advance in the clinical management of allograft receiving patients would be achieved if a method were developed whereby cytotoxic lymphocytes, and more specifically cytotoxic T lymphocytes (CTL) could be inhibited or eliminated, thereby achieving a "turning off" effect of already activated CTL participating and-/or contributing to an ongoing allograft rejection.

A variety of functional and phenotypic characteristics can be used to distinguish these various types of cytotoxic effector cells. However, a number of surface antigens and functional characteristics are shared. Thus, the antigens identified by the monoclonal antibodies OKT8;[23,24] and, OKT11;[24,25] NK9[26] and anti-D44[27] are found on both CTL and NK while the antigen identified by OKM1 is shared by MP and NK.[23,24,25,28] Furthermore, cytolytic activity of both NK and MP is augmented by interferons.[22,29,30] Finally, use of metabolic inhibitors has demonstrated some parallels in the lytic mechanism employed by CTL and NK.[9,10,31-34]

SUMMARY OF THE INVENTION

The present invention concerns certain dipeptide esters and their uses, particularly for ablation of certain cell-mediated immune responses. A most particularly pronounced aspect of the present invention provides for a method of inhibiting as well as preventing graft rejection. Most particularly the present invention provides for the inhibition of host skin allograft rejection with the dipeptide alkyl ester described herein. Even more particularly, the alkyl ester of the dipeptides found effective in inhibiting and preventing allograft rejection is an O-alkyl depeptide ester, for example, L-leucyl L-leucine.

An alkyl ester of dipeptides comprising, or most preferably consisting essentially of natural or synthetic L-amino acids with hydrophobic side chains is provided by the present invention. Preferable amino acids are leucine, phenylalanine, valine, isoleucine, alanine, proline, glycine or aspartic acid β-methyl ester. Preferable dipeptides are L-leucyl L-leucine, L-leucyl L-phenylalanine, L-valyl L-phenylalanine, L-leucyl L-isoleucine, L-phenylalanyl L-phenylalanine, L-valyl L-leucine, L-leucyl L-alanine, L-valyl L-valine, L-phenylalanyl L-leucine, L-prolyl L-leucine, L-leucyl L-valine, L-phenylalanyl L-valine, L glycyl L-leucine, L-leucyl L-glycine or L-aspartyl S-methyl ester L-phenylalanine. The most preferable dipeptides are L-leucyl L-leucine, L-leucyl L-phenylalanine, L-valyl L-phenylalanine, L-phenylalanyl L-leucine, L-leucyl L-isoleucine, L-phenylalanyl L-phenylalanine and L-valyl L-leucine.

The alkyl ester of the dipeptide is most preferably a methyl ester and may also be an ethyl ester or alkyl of up to about four carbon atoms such as propyl, isopropyl, butyl or isobutyl.

For brevity and clarity, many of the terms used herein have been abbreviated. These abbreviations appear at Table 1.

While not intending to be limited to any particular theory or mechanism of action, Applicants postulate in the present inventive methods that preventing and/or inhibiting allograft rejection is accomplished with the present methods through the inactivation of already activated CTL in vivo through the use of the described dipeptide alkyl esters. Particularly, the administration of the dipeptide alkyl ester Leu-Leu-OMe is postulated to effectively inhibit activated CTL to provide the prevention of allograft rejection demonstrated herein. However, other mechanisms of action whereby the described dipeptide alkyl esters elicit the demonstrated prevention and/or inhibition of allograft rejection may be contributing to the described therapeutic effects.

The following abbreviations (Table 1) are employed throughout the following description of the invention.

TABLE I

| Abbreviations | |
|---|---|
| Substance | Symbol |
| L-alanine | ala |
| L-arginine | arg |
| L-aspartic acid | asp |
| L-glutamic acid | glu |
| L-glycine | gly |
| L-isoleucine | ile |
| L-leucine | leu |
| L-lysine | lys |
| L-phenylalanine | phe |
| L-proline | pro |
| L-serine | ser |
| L-tyrosine | tyr |
| L-valine | val |
| D-amino acids methyl esters | e.g. D—Leu—OMe |
| D-amino acids | e.g. D—Leu |
| dipeptides of L-amino acids | e.g. Leu—Leu |
| L amino acid methyl esters | e.g. Leu—OMe |
| L amino acids | e.g. Leu—Leu—OMe |
| L amino acid ethyl esters | e.g. Leu—OEt |
| L-leucyl-L-leucine methyl ester | Leu—Leu—Ome |
| major histocompatibility complex | MHC |
| methyl esters of dipeptide | |
| Spleen cells | SpC |
| T cell depleted | TCD |
| cell fraction or type | |
| cytotoxic T-lymphocytes | CTL |
| glass or nylon wool non-adherent cells | NAC |
| glass or nylon wool adherent cells | AC |
| monoclonal antibodies | mAb |
| mononuclear phagocytes | MP |
| natural killer cells | NK |
| peripheral blood mononuclear cells | PBM |
| polymorphonuclear leucocytes | PMN |
| Other Materials | |
| dipeptidyl peptidase I | DPPI |
| fluorescence activated cell sorter | FACS |
| fluorescene activated cell sorter | FACS |
| mixed lymphocyte culture | MLC |
| phosphate buffered saline | PBS |
| thin layer chromatography | TLC |

TABLE I-continued

| Abbreviations | |
|---|---|
| | Symbol |
| Miscellaneous | |
| adult thymectomized and bone marrow reconstituted mice | ATXBM |
| difference (Student's t-test) | p |
| effector:target cell ratio | E:T |
| fetal bovine serum | FBS |
| Graft versus host disease | GVHD |
| Standard error of mean probability of significant | SEM |
| University of Texas Health Science Center, Dallas, Texas. | UTHSCD |

BRIEF DESCRIPTION OF THE DRAWINGS

FIG. 10A: Thymectomized B6D2F1 Recipients; FIG. 10B: Control B6D2F1 Recipients.

DETAILED DESCRIPTION OF PREFERRED EMBODIMENTS

Figure 1:
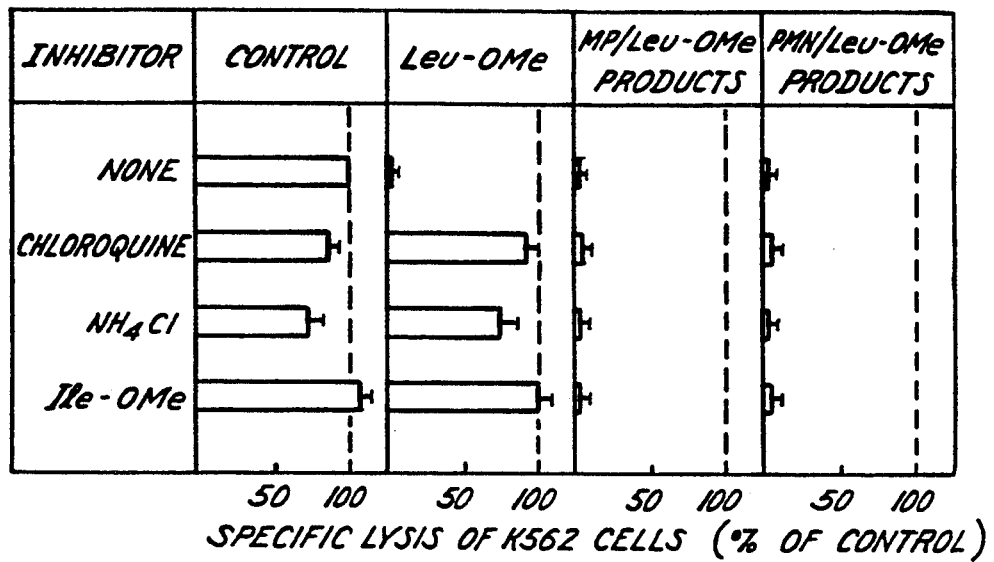
FIG. 1 shows that whereas ablation of NK function during incubation with Leu-OMe can be blocked by lysosomotropic agents, there is a product formed during incubation of Leu-OMe with MP or PMN which has effects on NK function no longer blocked by lysosomal inhibitors.

The present invention concerns new compounds and their uses in ablating particular cell types and their functions. The presently described invention relates to the discovery that dipeptide alkyl esters are cytotoxic metabolites of lysosomotropic amino acid alkyl esters.

It has further been found that alkyl esters of dipeptides consisting essentially of natural or synthetic amino acids with hydrophobic side chains may function cytotoxically to deactivate natural killer cells (NK) and cytotoxic T lymphocytes (CTL). By the term "hydrophobic" as used herein, is meant uncharged in aqueous solution at physiological pH and also as having no hydroxyl, carboxyl or primary amino groups.

Treatment of NK or CTL with an effective level of an alkyl ester of a dipeptide consisting essentially of natural or synthetic amino acids with hydrophobic side chains serves to deactivate the cytotoxic functions of the cells. An "effective level" will vary from circumstance to circumstance but generally lies between about 25 μM and about 250 μM. An effective level for a whole animal dose generally lies between about 100 mg/kg and about 300 mg/kg.

Both methyl and ethyl esters of dipeptides consisting essentially of natural or synthetic amino acids having hydrophobic side chains have been specifically found to deactivate natural killer cells or cytotoxic T lymphocytes. Other alkyl esters of these dipeptides are confidently predicted to have similar or superior effects.

Deactivation of natural killer cells (NK) or CTL cells with such dipeptide alkyl esters should increase the success of allogeneic bone marrow transplants by lowering the incidence of graft-versus-host disease (GVHD) and by lowering the incidence of transplant rejection.

Graft versus host disease (GVHD) is a major problem in allogeneic bone marrow transplantation. It occurs in approximately 70% of transplant recipients and causes death in 20% of those.[35] The disease occurs when cells of the graft (donor) attack the host tissue, causing abnormalities in the immune system and gastrointestinal tract, as well as skin rashes and liver dysfunction. Although cytotoxic T lymphocytes have traditionally been considered to be the primary effector cells in GVHD, recent studies have shown a correlation between the occurrence of the disease and the appearance of NK activity soon after transplantation. These results implicate the donor's NK cells in the etiology of GVHD. Moreover, other studies demonstrate that high levels of NK activity in a bone marrow recipient prior to transplantation are associated with GVHD.[36-38] Thus, it is theorized that both host and donor NK cells contribute to the development of the disease.

Current regimens for the prevention and treatment of GVHD consist of depleting T-lymphocytes from the donor marrow prior to transplantation and giving the recipient immunosuppressive drugs such as cyclophosphamide and methotrexate, both before and after transplantation. The effectiveness of these regimens might be enhanced by treating donor bone marrow and transplant recipients with the dipeptide methyl esters described according to the present invention. Potential problems with these procedures include possible non-specific toxicity of therapeutic dipeptide alkyl esters and the re-emergence of NK activity from precursors not sensitive to therapeutic dipeptide alkyl esters.

Currently, bone marrow transplantation is used as a major mode of therapy in treating aplastic anemia, acute myelogenous leukemia, and a variety of immunodeficiency states. As mentioned above, a major complication of this therapy is graft-versus-host disease.[39] Severity of GVHD in man correlates with pretransplant levels of natural killer (NK) activity.[40] Thus, by virtue of its ability to diminish NK function in vivo, it is contemplated that Leu-Leu-OMe administration, for example, to bone marrow samples prior to their transplantation will be efficacious in diminishing this complication. An effective level of the dipeptide alkyl esters of the present invention for in vitro deactivation of natural killer cells is between about 10 μM and about 250 μM.

Furthermore, in both murine and human models, the incidence of GVHD is decreased by in vitro treatment of donor bone marrow with agents that deplete mature T cells.[41,42] Since cytotoxic T cells (CTL) derived from donor bone marrow appear to be the final mediators of GVHD, in vitro treatment of donor bone marrow with an agent which selectively damages cytotoxic T cell precursors is also likely to be of benefit. Since such an in vitro action of Leu-Leu-OMe has now been demonstrated, it is expected that this agent will be of benefit in pre-treating donor bone marrow according to the methods described for the present invention. An effective level of the dipeptide alkyl esters of the present invention for treatment of bone marrow to be transplanted should be between about 10 μM and 250 μM for ablation of GVHD-mediating CTL and NK.

A second problem in bone marrow transplantation is the failure of engraftment (the transplant does not "take" or is rejected). This problem occurs in 10–20% of transplants and can be caused by several factors, including improper transplantation technique, extensive invasion of the recipient's bone marrow by tumor cells, and rejection of the transplant.

The discovery that F[1] mice could reject transplants of parental bone marrow first indicated that NK cells might be involved in the engraftment failures.[43,44] Initially, graft rejection was thought to be almost totally dependent on T lymphocytes. However, T cells from an F[1] hybrid animal do not normally attack parental tissue. Therefore, it was suggested that NK cells, not T cells, mediated the rejection of the parental bone marrow.

Additional support for the above hypothesis regarding NK cells is derived from the observation that mice of a strain normally incapable of rejecting bone marrow transplants acquire this ability when they are injected with cloned NK cells.[45] As a result of these findings, Herberman, et al.[46] have suggested that suppression of NK activity might lower the incidence of transplant rejection. This suppression should be achieved by treating the recipient with the dipeptide methyl esters and most particularly those O-alkyl esters, of the present invention, prior to transplantation.

Other clinical uses for alkyl esters of dipeptides consisting essentially of amino acids with hydrophobic side chains, are those situations where NK or CTL are involved in the pathogenesis of disease. In organ transplants in general (kidney, heart, liver, pancreas, skin, etc.), it is widely accepted that cytotoxic T cells are likely to be the cell type responsible for graft rejection.[47]

It is demonstrated in the present disclosure that the in vivo administration of Leu-Leu-OMe, and perhaps also similar dipeptide esters, functionally inhibits the activity of DPPT-enriched cytotoxic lymphocytes. The data also demonstrates that ex vivo elimination of Leu-Leu-OMe sensitive cytotoxic lymphocytes prolongs skin graft survival. These observations together suggests to the present inventors that Leu-Leu-OMe, and possibly other derivitives thereof, may be of benefit in preventing allograft rejection. The present invention provides a method for inhibiting and/or preventing the rejection of a tissue graft by an animal. As such, the present invention may also provide a method of inhibiting the rejection of whole tissue and organ transplants transplanted into an animal through treatment of the animal with the described dipeptide alkyl esters consisting of L-amino acids with hydrophobic side chains.

In a most preferred embodiment, the method of inhibiting the rejection of a tissue graft by an animal comprises treating the animal with a therapeutically effective amount of an alkyl ester of a dipeptide consisting essentially of the L-amino acids leucine, phenylalamine, valine, isoleucine, alamine, proline, glycine, or aspartic acid β-methyl ester, individually or in combination. Most preferably, the alkyl ester of a dipeptide is administered in a pharmaceutically acceptable diluent or carrier. The present methods are expected to be effective in preventing rejection of tissue grafts of all types such as, for example, skin grafts. The rejection of tissue skin grafts is effectively prevented and/or inhibited in animals described in the examples herein. For example, skin allograft survival time is demonstrated herein to be improved 82% over non-treated controls (17 days vs 31 days) upon treatment according to the claimed methods.

It is also contemplated that Leu-Leu-OMe or other similar alkyl dipeptide esters may be of benefit in other spontaneously occurring disease states. A variety of diseases have been classified as "autoimmune diseases" because of the widely accepted belief that they are caused by disorders in the immune system which cause immunologic damage to "self". Thus, in a variety of diseases, including primary biliary cirrhosis, systemic lupus erythematosus, rheumatoid arthritis, multiple sclerosis, autoimmune hemolytic anemia, etc., various forms of immunologic damage to selected organs occur. In some of these diseases, such as primary biliary cirrhosis, the histologic abnormalities which occur (in this case in the liver) closely resemble those which occur in GVHD or in rejection of a transplanted liver.[48] Thus, it is reasonable that similar mechanisms of cytotoxic lymphocyte damage to liver cells may be occurring, and therefore may also benefit from therapy with Leu-Leu-OMe or other of the dipeptide alkyl esters of the present invention.

The dipeptide alkyl esters of the present invention should be usable with chemotherapeutic agents in patients with natural killer cell tumors (generally leukemias), although very few reports of these tumors are found in the literature.[49,50,51]

It is contemplated that the dipeptide alkyl esters of the present invention may also be used to treat patients with aplastic anemia and other types of bone marrow dysfunction. This suggestion is based on three sets of observations in human studies: first, NK cells can kill normal bone marrow cells;[52] second NK cells inhibit growth of blood cell precursors in vitro;[53,54,55,56] and third, NK-like cells with the ability to inhibit the formation of red blood cells have been isolated from patients with aplastic anemia.[57,58] Moreover, recent studies in the mouse indicate that NK cells may function to suppress hemopoiesis in vivo.[59] However, further investigation is desireable before the connection between NK activity and bone marrow dysfunction is considered conclusive.

Generally, when the dipeptide alkyl esters of the present invention are administered to animals, an effective level is between about $1 \times 10^{-4}$ moles/kg and about $1 \times 10^{-2}$ moles/kg.

The following Examples are presented to more fully illustrate preferred embodiments of the present invention and are not intended to limit the invention, unless otherwise so stated in the accompanying claims.

EXAMPLE 1

Cell Preparations and Assays

PBM were separated from heparinized venous blood of healthy donors by centrifugation over sodium diatrizoate-Ficoll gradients (Isolymph, Gallard-Schlesinger Chemical Mfg. Corp., Carle Place, N.Y.). Monocyte-enriched populations ((MP) were prepared from glass adherent cells and MP-depleted lymphocytes from the nonadherent cells remaining after incubation in glass Petri dishes and passage through nylon wool columns as detailed in Rosenberg et al. (1975).[60] PMN were collected by resuspending peripheral blood cells that penetrated sodium diatrizoate-Ficoll gradients and removing erythrocytes by dextran sedimentation and hypotonic lysis as previously outlined.[61]

All cell exposures to the amino acids, dipeptides or their methyl esters were carried out by suspending cells in Dulbecco's phosphate buffered saline (PBS) and incubating them at room temperature with the reagent at the indicated concentration and time interval. After incubation, the cells were washed twice with Hanks' balanced salt solution and resuspended in medium RPMI 1640 (Inland Laboratories, Fort Worth, Tex.) supplemented with 10% fetal bovine serum (Microbiological Associates, Walkersville, Minn.) for assay of function.

Natural killing against K562 target cells was assessed by a 3 hour $^{51}$Cr release assay and percent specific lysis calculated as previously described.[61] Percent of control cytotoxicity was calculated using the formula:

$$\frac{\text{Experimental \% specific lysis}}{\text{Control \% specific lysis}} \times 100$$

EXAMPLE 2

General Procedures for Generation, Purification and Characterization of L-leucine Methyl Ester and Its Metabolites MP or PMN (prepared as in Example 1) at a concentration of $25 \times 10^6$ per ml were suspended in PBS and incubated with 25 mM Leu-OMe for 20 minutes at 22° C. Cell suspensions were then centrifuged at 1000 g for 10 minutes and the supernatants harvested and freeze-dried at −70° C., 100 millitorr atmospheric pressure. In some experiments, Leu-OMe-treated MP or PMN were sonicated to increase the yield of the reaction product. Samples were then extracted with methanol for application to thin layer chromatography (TLC) plates (200 micromolar×20 cm$^2$, Analtech, Newark, Del.). Following development with chloroform/methanol/acetic acid (19:1:12.5 by volume), 1 cm bands were eluted with methanol, dried under nitrogen, and resuspended in 1 ml PBS. Mass spectra were obtained with a Finnegan Model 4021 automated EI/CI, GC/MS system coupled to an Incos data system. Methane was used as the reagent gas for chemical ionization (CI)mass spectral analysis.

EXAMPLE 3

Lysosomotropic Substances and Formation of NK-toxic Products

The addition of Leu-OMe to human PBM was shown to cause rapid death of MP and NK cells but not T or B lymphocytes.[1,61] Amino acid methyl esters are known to be lysosomotropic compounds, and in previous studies it was found that the lysosomal inhibitors, chloroquine and $NH_4Cl$, prevented Leu-OMe-induced MP toxicity. To assess whether these agents similarly prevented formation of any NK toxic products, the following experiments were carried out, and the results shown in FIG. 1.

PBM (prepared as in Example 1) were incubated with various potential NK toxic agents in the presence or absence of various lysosomal inhibitors for 40 minutes, washed to remove the inhibitor, incubated for 18 hours to permit recovery from any transient inhibition caused by lysosomotropic agents and then tested for NK activity. As can be seen in FIG. 1, neither chloroquine, $NH_4Cl$, nor Ile-OMe had any substantial permanent effect on NK function. In contrast, 5 mM Leu-OMe ablated all NK activity. This activity of Leu-OMe was largely prevented by chloroquine, $NH_4Cl$, or Ile-OMe. The products generated by MP or PMN, after exposure to Leu-OMe also completely removed all NK activity from PBM. In contrast to the effect noted with Leu-OMe, the lysosomal inhibitors did not protect NK cells from the action of this product(s). Additional experiments indicated that the sonicates of MP or PMN had no effect on NK function in this system whereas the supernatants or sonicates of Leu-OMe treated PMN or MP also depleted NK cells from MP depleted lymphocytes. These results therefore suggest that interaction of Leu-OMe with the lysosomal compartment of MP or PMN produced a product which was directly toxic to NK cells through a mechanism that was no longer dependent on lysosomal processing within the NK cell or an additional cell type.

More particularly, the conditions of the manipulations leading to the results shown in FIG. 1 were as follows:

Inhibitors of lysosomal enzyme function prevent generation of an NK toxic product. PBM ($5 \times 10^6$/ml) or PMN ($25 \times 10^6$/ml) preincubated with 25 mM Leu-OMe for 30 minutes were added to cells to be ablated. Cells were incubated with these agents for another 30 minutes at 22° C., then washed and cultured for 18 hours at 37° C. before assay of the ability to lyse K562 cells. Data are expressed as percentage of control cytotoxicity observed with an effector:target ratio of 40:1 (results at other E:T were similar). These results demonstrated that whereas ablation of NK function during incubation with leu-OMe can be blocked by lysomotropic agents, there is a product formed during incubation of Leu-OMe with MP or PMN which has effects on NK function no longer blocked by lysosomal inhibitors.

EXAMPLE 4

Ablation of NK Function by PMN produced Leu OMe Product in vitro

Figure 2:
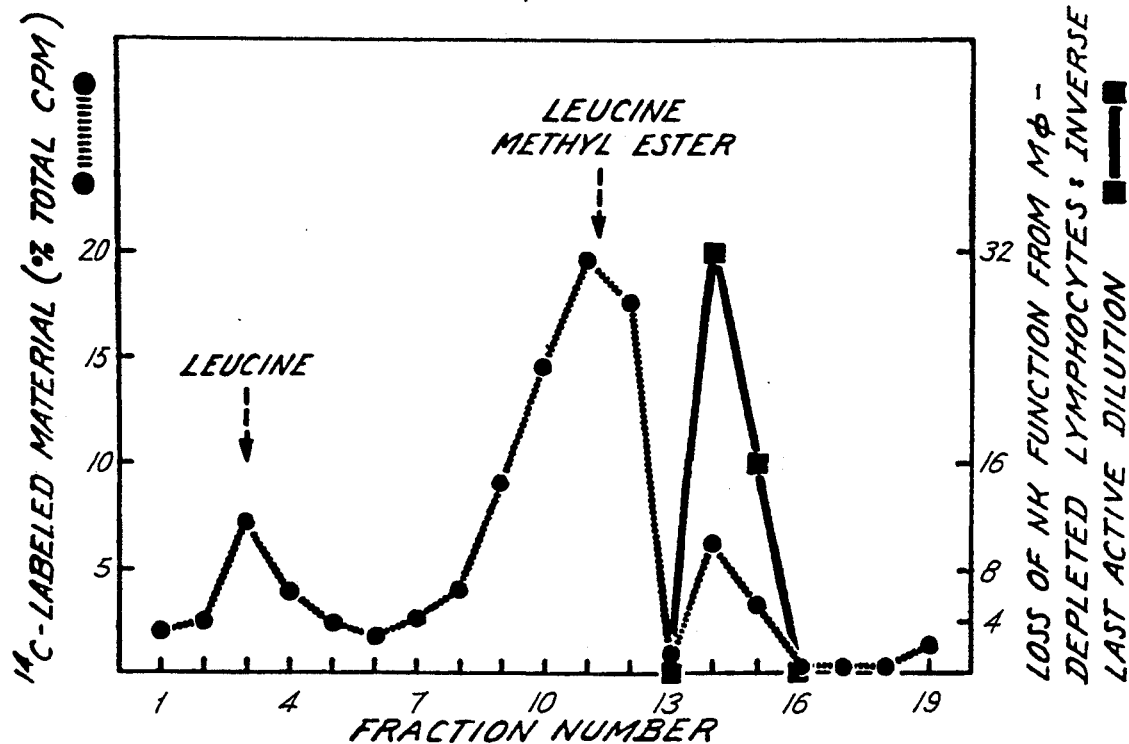
FIG. 2 shows Leu-OMe products of PMN in terms of radioactivity and NK suppressive effects of TLC fractions.

When the NK toxic properties of MP-Leu-OMe, or PMN-Leu-OMe incubation mixtures were evaluated, it was found that this activity was stable in aqueous solutions for more than 48 hours at 4° C., but labile at 100° C., retarded on Sephadex G-10 columns; dialyzable through 1000 MWCO (molecular weight cut-off) membranes, and could be extracted by chloroform-methanol (3:1, by volume). As shown in FIG. 2, when $^{14}C$-leucine methyl ester was incubated with PMN and the supernatants subsequently separated by TLC, three major peaks of $^{14}C$ activity were found. One of these peaks corresponded to leucine methyl ester itself and one to free leucine while the third represented a new product. This third peak accounted for about 10% of the total $^{14}C$-labeled material. When MP-depleted lymphocytes were exposed to each TLC fraction, the third peak was found to contain all NK toxic activity. This NK toxic activity not only appeared to be $^{14}C$ labeled but was also ninhydrin positive, suggesting that it was a metabolite which still retained an amino group as well as part of the carbon structure of Leu-OMe. An identical $^{14}C$ labeled ninhydrin positive product was detected by TLC of MP-Leu-OMe incubation mixture supernatants or sonicates. The production by PMN or MP of this metabolite was inhibited by chloroquine, $NH_4Cl$, or Ile-OMe (data not shown).

Ablation of NK function is mediated by a metabolite of Leu-OMe. PMN ($25 \times 10^6$/ml) were incubated with 25 mM $^{14}C$-Leu-OMe for 30 minutes and supernatants harvested for TLC analysis. MP-depleted lymphocytes ($2.5 \times 10^6$ cells/ml) were exposed to varying dilutions of each TLC fraction for 30 minutes, washed and cultured for 2 hours prior to cytotoxicity assay at E:T ratio of 20:1. Samples were considered to contain an NK toxic product when percent specific lysis was less than 25% of control. FIG. 2 shows these results.

EXAMPLE 5

Characterization Of The NK-toxic Metabolite

Figure 3A:
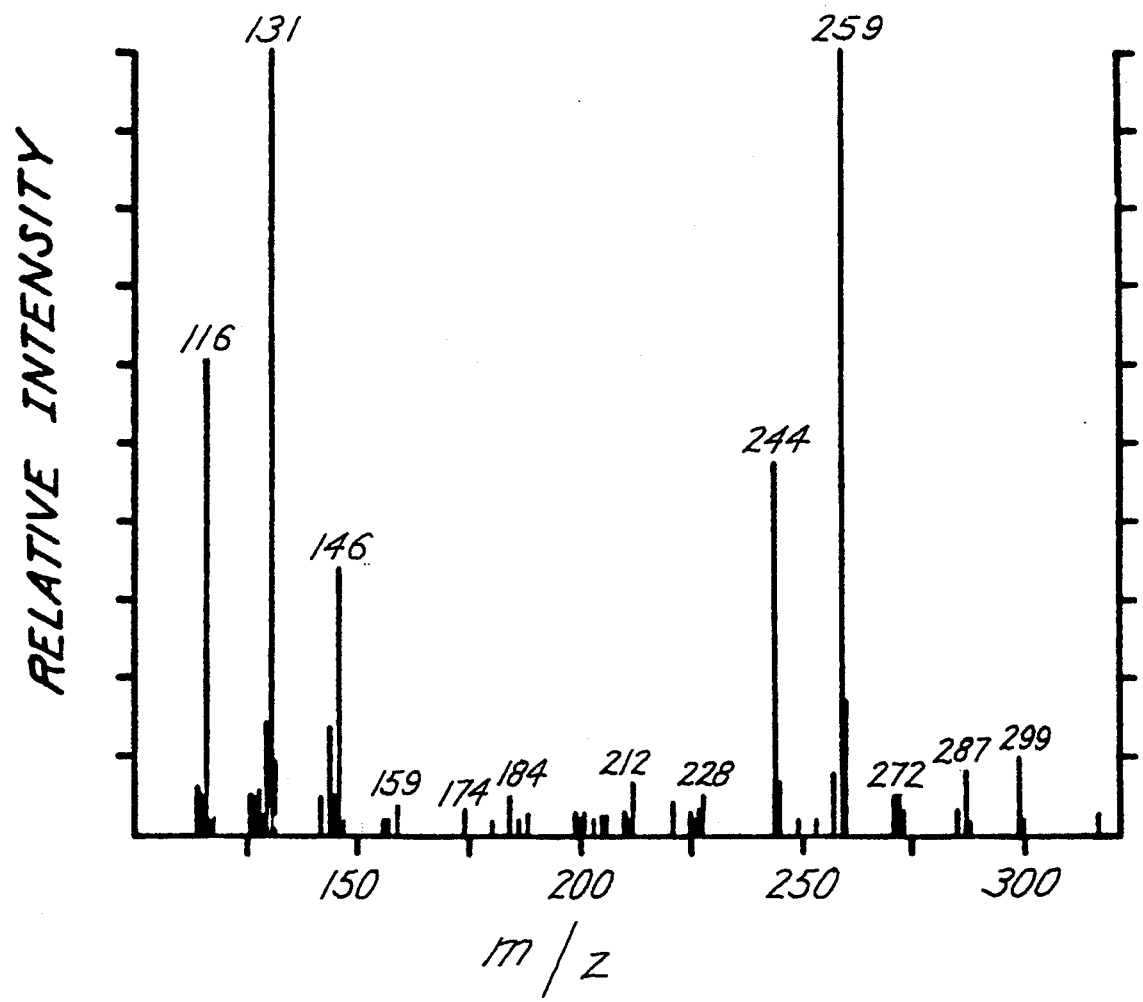
FIGS. 3A and 3B show the CI mass spectra of TLC fractions with NK toxic activity and of synthetic Leu-Leu-OMe.

The nature of the new TLC peak found as described in Example 4 was examined by mass spectroscopy. As shown in FIG. 3A, when the TLC-purified, NK-toxic fraction was subjected to more spectral analysis, results (MN+), 287 (M+$C_2H_5$+) and 299 (M+$C_3H_5$+)) indicated the presence of a compound of molecular weight 258. The presence of peaks at M/Z 244 (M+—$CH_3$) and 272 (M+$C_2H_55$+—$CH_3$) suggested that this compound contained a methyl ester group. Furthermore, the persistence of peaks corresponding to leucine (MN+=131, M+$C_2H_5$=159) and leucine methyl ester (MH+=146, M+$C_2H_5$+=174) in spite of careful TLC purification of the NK toxic product from any free leucine or Leu-OMe present in the crude supernatants of the incubation mixtures suggested that a condensation product of Leu-OMe such as Leu-Leu-OMe (MW258) was present in the NK toxic fraction isolated after incubation of PMN or MP with Leu-OMe.

When Leu-Leu-OMe was synthesized from reagent grade Leu-Leu, by incubation in methanol hydrochloride, it was found to have TLC mobility identical to NK toxic fractions of MP-Leu-OMe or PMN-Leu-OMe incubation mixtures. Furthermore, its CI mass spectrum as shown in FIG. 3B was identical to that of the 258 molecular weight compound found in these incubation fractions.

Experiments further confirmed that Leu-Leu-OMe was the product generated by MP or PMN from Leu-OMe that was responsible for the selective ablation of NK function from human lymphocytes. Leu-Leu-OMe was synthesized by addition of Leu-Leu to methanolic HC1. TLC analysis revealed less than 2% contamination of this preparation with leucine, Leu-Leu, or leu-OMe, and CI mass spectral analysis (FIG. 3B) revealed no contaminants of other molecular weights.

Figure 3B:
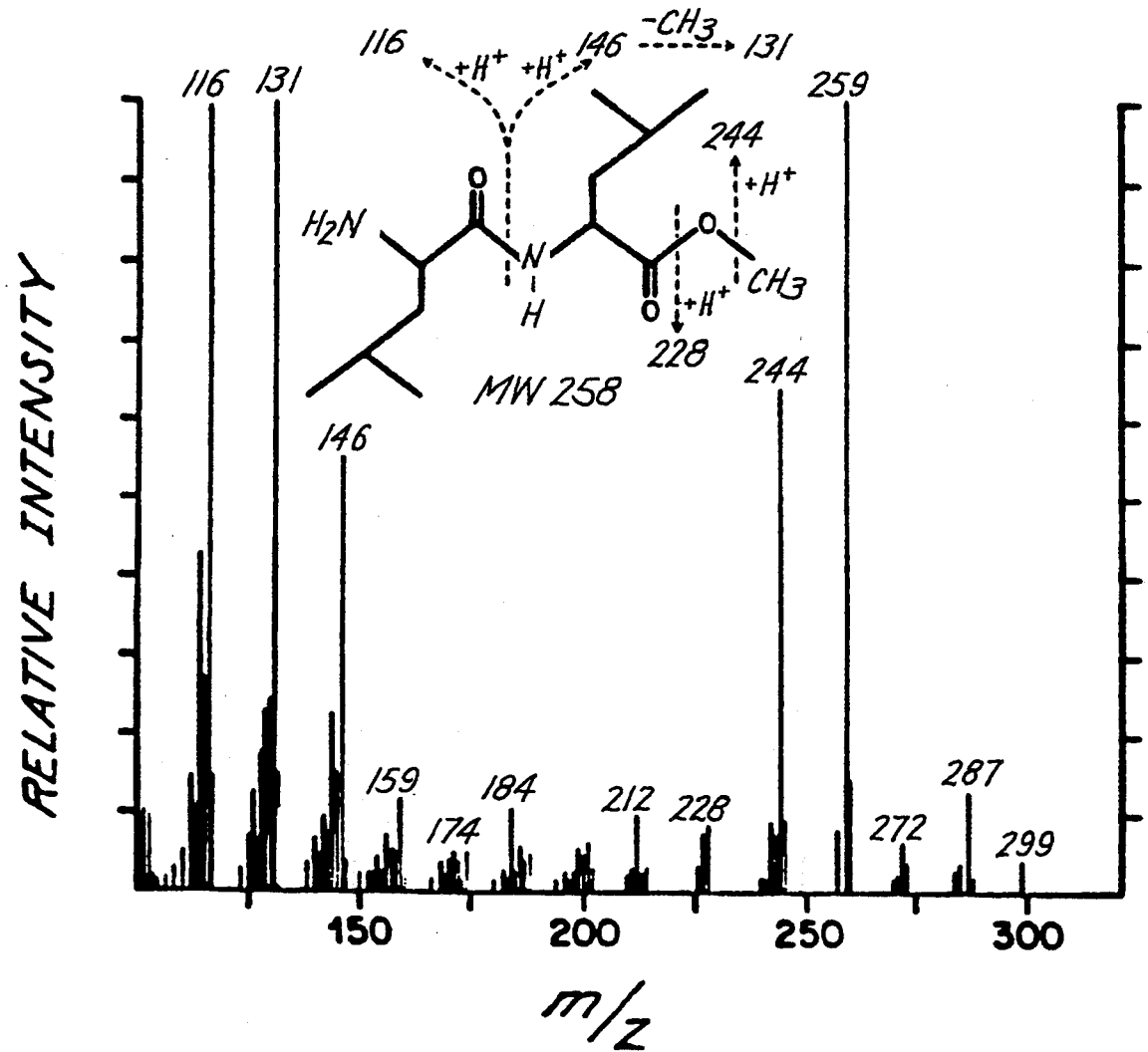

FIG. 3A shows the chemical-ionization CI mass spectra of TLC fractions with NK toxic activity as described in FIG. 2, and also of Leu-Leu-OMe synthesized from reagent grade Leu-Leu (FIG. 3B).

EXAMPLE 6

Effect of Dipeptide and Tripeptide Methyl Esters on NK Functions

Figure 4A:
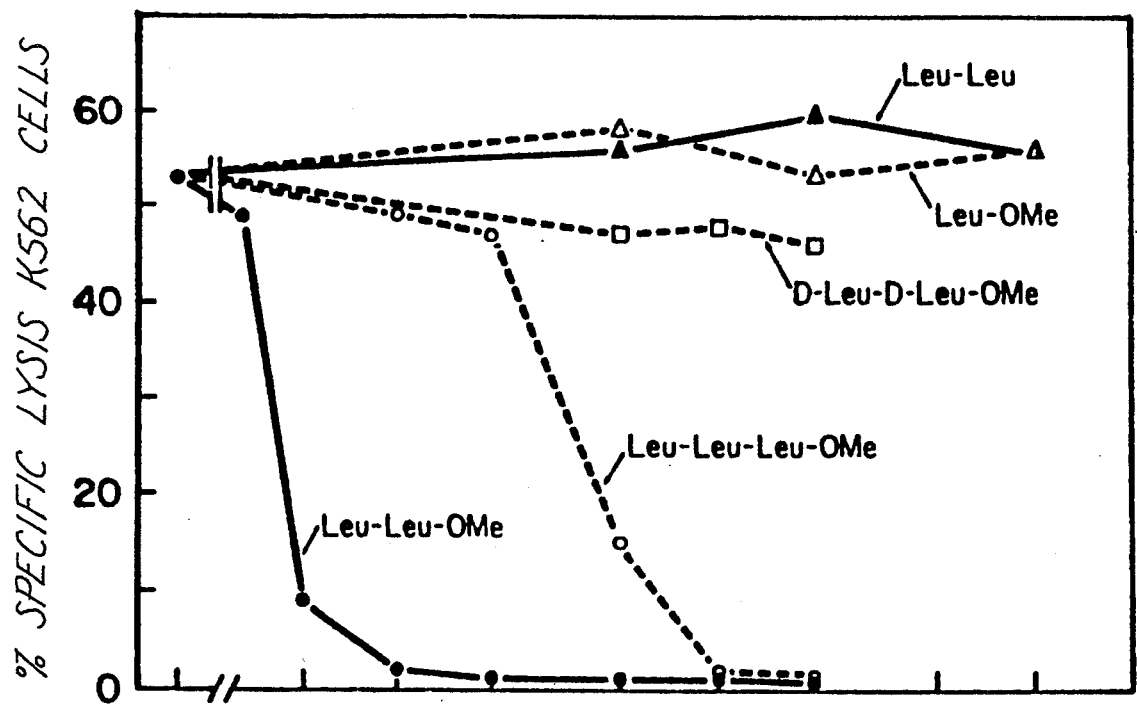
FIGS. 4A and 4B show the effects of various agents on losses of NK function from MP-depleted lymphocytes.
Figure 4B:
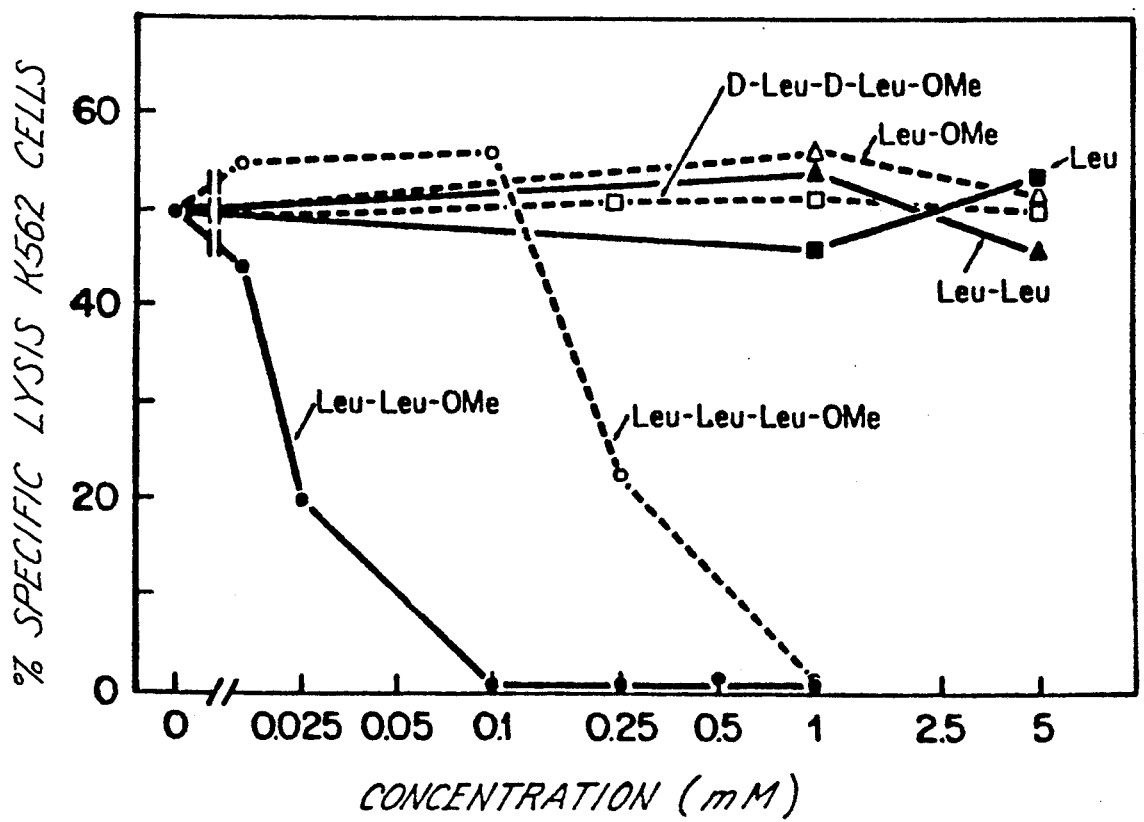

In the representative examples shown in FIGS. 4A and 4B, MP-depleted lymphocytes were exposed to varying concentrations of Leu-Leu-OMe for 15 minutes at room temperature, then washed and assayed for ability to lyse K562 cells. No NK function could be detected in lymphocyte populations exposed to greater than 50 μM (micromolar) Leu-Leu-OMe. As previously demonstrated,[1] exposure of such MP-depleted lymphocyte populations to a 100-fold greater concentration of leucine or leu-OMe had no irreversible effect on NK function. Leu-Leu or the D-stereoisomer, D-Leu-D-Leu-OMe, also had no inhibitory effect.

While Leu-Leu-Leu-OMe caused dose-dependent loss of NK function, 5-fold greater concentrations of this tripeptide methyl ester were required to cause an effect equivalent to that of the dipeptide methyl ester of L-leucine. When lymphocyte populations exposed to varying concentrations of Leu-Leu-OMe were further analyzed, it was found that exposure to more than 50 μM Leu-Leu-OMe resulted in the loss of K562 target binding as well as complete depletion of cells stained by Leu 11b, and anti-NK cell monoclonal antibody (data not shown). Thus, the MP-or PMN-generated product of Leu-OMe which is directly toxic for human NK cells is the dipeptide condensation product Leu-Leu-OMe.

The condition of the manipulations resulting in the data leading to FIGS. 4A and 4B are further detailed as follows: for loss of NK function after exposure to Leu-Leu-OMe, MP-depleted lymphocytes ($2.5 \times 10^6$ cells/ml) were incubated for 15 minutes with the indicated concentrations of leucine containing compounds. Cells were then washed, cultured at 37° C. for 2 hours (Expt. 1) or 18 hours (Expt. 2) and then assayed for NK activity. Results are given for E:T ratio of 20:1.

EXAMPLE 7

NK Ablation by a Variety of Dipeptide Methyl Esters

In previously reported studies, Leu-OMe was unique among a wide variety of amino acid methyl esters in its ability to cause MP or PMN dependent ablation of NK cell function from human PBM.[61] The identification of Leu-Leu-OMe as the MP-generated metabolite responsible for this phenomenon suggested that either MP/PMN did not generate the corresponding dipeptide methyl esters in toxic amounts from other amino acids, or that Leu-Leu-OMe was unique among dipeptide methyl esters in its toxicity for NK cells. Therefore, experiments were carried out to assess the effect of other dipeptide methyl esters on NK cell function. The methyl esters of a variety of dipeptides were synthesized and analyzed for the capacity to deplete NK cell function. Each dipeptide methyl ester was assessed in a minimum of three experiments.

Figure 5:
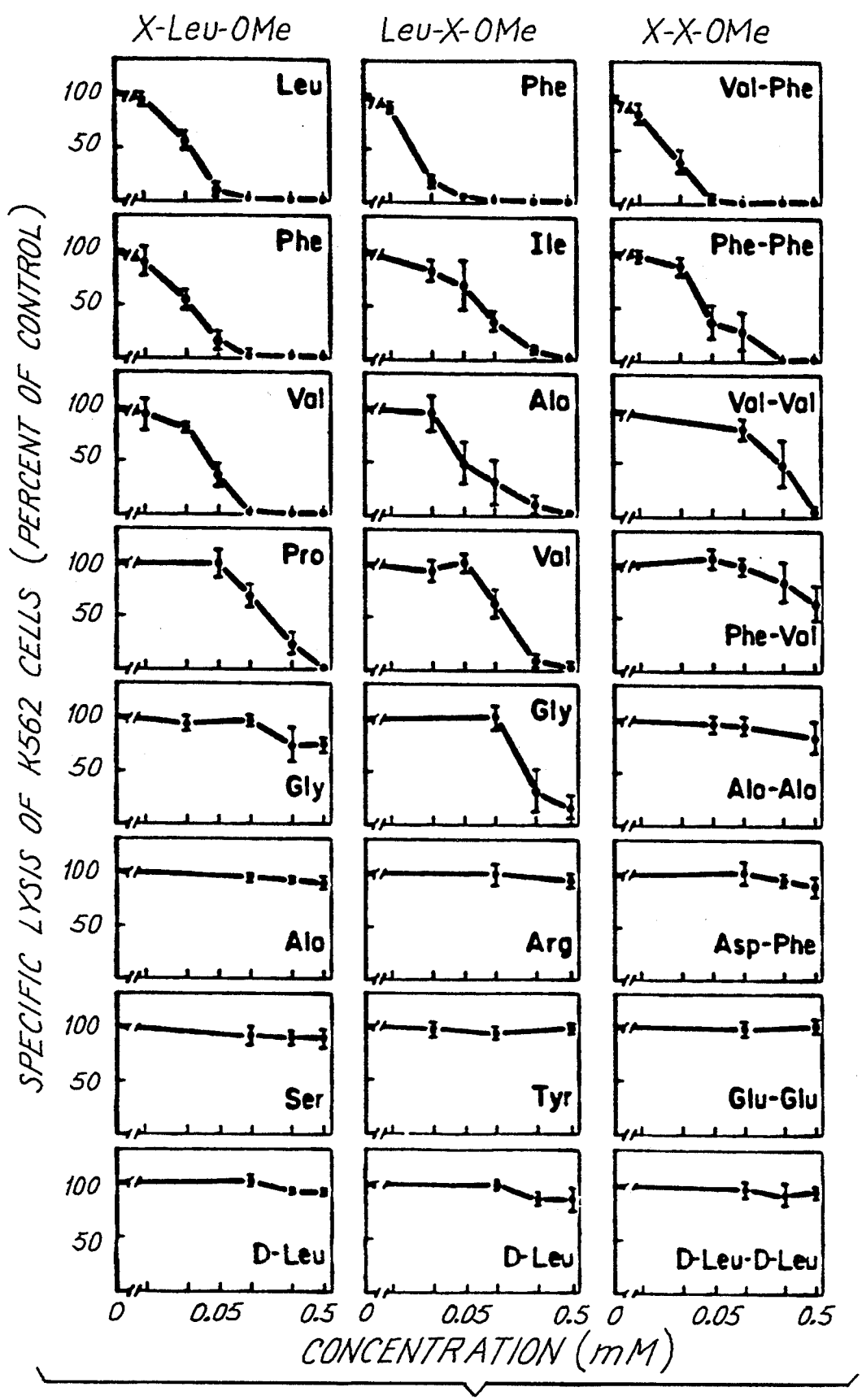
FIG. 5 shows the NK-toxicity of various dipeptide esters.

As is shown by the results displayed in FIG. 5, Leu-Leu-OMe is not the only dipeptide methyl ester which exhibits NK toxicity. When amino acids with hydrophobic side chains were substituted for leucine in either position, the resulting dipeptide methyl ester generally displayed at least some degree of NK toxicity. In particular, Leu-Phe-OMe, Phe-Leu-OMe, Val-Phe-OMe, and Val-Leu-OMe produced concentration-dependent ablation of NK function at concentrations comparable to those at which Leu-Leu-OMe was active.

The sequence of active amino acids was important, however, as evidenced by the finding that Phe-Val-OMe was markedly less active than Val-Phe-OMe. Similarly, Leu-Ala-OMe was NK inhibiting, whereas 10-fold greater concentrations of Ala-Leu-OMe had no NK inhibitory effects. Furthermore, Phe-Phe-OMe was less NK toxic than either Leu-Phe-OMe or Phe-Leu-OMe and Val-Val-OMe was less active than either Leu-Val-OMe or Val-Leu-OMe, yet Val-Phe-OMe was among the most potent of the NK toxic dipeptide methyl esters. Thus, conformational aspects of the dipeptide methyl ester amino acid side chain also seem to be of importance in producing the different levels of observed NK toxicity.

When amino acids with hydrophilic, charged or hydrogen side chains were substituted for leucine, the resulting dipeptide methyl esters either had greatly reduced NK toxicity, as in the case of Gly-Leu-OMe or Leu-Gly-OMe, or no observed NK inhibitory effects, as in the case of Leu-Arg-OMe, Leu-Tyr-OMe, Ser-Leu-OMe, Lys-Leu-OMe or Asp-Phe-OMe. Furthermore, when the D-stereoisomer was present in either position of a dipeptide methyl ester, no toxicity was observed for NK cells (FIG. 5). When unesterified dipeptides were assessed for their effect on NK function, as in the case of Leu-Leu (FIGS. 4A and 4B), up to $5 \times 10^{-3}$ M concentrations of Leu-Phe, Phe-Leu, Val-Leu, and Val-Phe had no effect on NK cell survival or lytic activity (data not shown).

D-Leu-D-Leu-OMe had no effect on Leu-Leu-OMe mediated NK toxicity although high levels of zinc appeared to inhibit this Leu-Leu-OMe toxicity.

Previous experiments had demonstrated that compounds such as Val-OMe, Phe-OMe, or combinations of Val-OMe and Phe-OMe did not delete NK function from human PBM,[61] despite the current finding that dipeptide methyl esters containing these amino acids were potent NK toxins. In order to determine whether MP or PMN could generate the relevant dipeptide methyl esters from these amino acid methyl esters, TLC analysis of the supernatants of MP and PMN incubated with these compounds was carried out. It was found that MP and PMN did generate detectable amounts of dipeptide methyl esters from these L-amino acid methyl esters. However, when equal concentrations of Leu-OMe, Val-OMe, or Phe-OMe were added to MP or PMN, the concentrations of Val-Val-OMe generated were 50 to 80% of those found for Leu-Leu-OMe, while Phe-Phe-OMe was detected at only 10–30% of the levels of Leu-Leu-OMe. Dipeptide methyl esters were not generated from D-amino acid methyl esters.

FIG. 5 shows the NK toxicity of dipeptide methyl esters. MP-depleted lymphocytes were treated with varying concentrations of dipeptide methyl esters as outlined in FIGS. 4A and 4B. Results are given for the mean ±SEM of at least 3 separate experiments with each compound.

EXAMPLE 8

NK Toxicity of an Artificially Hydrophobic Dipeptide Methyl Ester

β-methyl aspartyl phenylalanine was prepared by methanolic hydrochloride methylation of aspartyl phenylalanine methyl ester. The NK toxicity of both aspartyl phenylalanine methyl ester and β-methyl aspartyl phenylalanine methyl ester was measured as described for the dipeptide methyl esters in Example 7. As the data in Table 2 indicates, when the polar side chain of the aspartyl amino acid dipeptide component is esterified with a methyl group, this being a conversion from relative hydrophilicity to substantial hydrophobicity, NK toxicity becomes apparent. Although yet not as toxically effective as a number of the hydrophobic-type dipeptides in Example 7, the data in Table 2 indicate that a dipeptide methyl ester comprising synthetic hydrophobic (lipophilic) amino acids may be used to inhibit NK function.

TABLE 2

L-ASPARTYL (β-METYHYL ESTER)-L-PHENYLALANINE METHYL ESTER IS NK TOXIC WHILE L-ASPARTYL-L-PHENYLALANINE METHYL ESTER IS NOT

| Preincubation | NK Function % Specific Cytotoxicity |
|---|---|
| Nil | 50.8 |
| Asp—Phe—OMe: | |
| 100 micromolar | 54.2 |
| 250 micromolar | 45.7 |
| 500 micromolar | 45.7 |
| 1000 micromolar | 46.9 |
| Asp—(βOMe)—Phe—OMe: | |
| 100 micromolar | 38.9 |
| 250 micromolar | 13.9 |
| 500 micromolar | 2.8 |
| 1000 micromolar | −0.1 |

EXAMPLE 9

In Vivo Effects of Dipeptide Alkyl Esters on Cytotoxic Cell Function

Leu-Leu-OMe or Leu-Phe-OMe were suspended in PBS, H 7.4. Individual C3H/HeJ mice (25 gram size) were then administered by tail-vein injection either $2.5 \times 10^{-5}$ moles (6.5 mg) of Leu-Leu-OMe, $2.5 \times 10^{-5}$ moles (7.1 mg) Leu-Phe-OMe, or an equal volume of the PBS diluent, this dose being about $1 \times 10^{-3}$ moles per kg. For 15–30 minutes post-injection, Leu-Leu OMe and Leu-PHe OMe-treated animals but not the control animals exhibited decreased activity and an apparent increase in sleep. Subsequent to this quiescent period no difference in activity or appearance in the mice was noted. Two hours post-injection, the mice were sacrificed and their spleen cells were assayed for NK function in a standard 4 hour assay against YAC-1 tumor targets. In all mice, total cell recovery ranged from $1 \times 10^8$ to $1.1 \times 10^8$ spleen cells per animal. As noted in Table 3, the control mouse spleen cells exhibited greater killing at 25:1 and 50:1 effector to target cell ratios than did the spleen cells of treated mice at 100:1 and 200:1 E/T, respectively. Thus, Leu-Leu-OMe or Leu-Phe-OMe caused a greater than 75% decrease in splenic lytic activity against YAC-1 tumor targets.

TABLE 3

| | Cytotoxic Cell Function | | | |
|---|---|---|---|---|
| | Effector:Target Ratio | | | |
| Percent lysis of target cells | 25:1 | 50:1 | 100:1 | 200:1 |
| Control | 8.29 | 12.88 | 20.60 | 29.29 |
| Leu—Leu—OMe | 2.37 | 4.58 | 7.12 | 12.77 |
| Leu—Phe—OMe | 3.89 | 4.68 | 6.91 | 11.91 |

EXAMPLE 10

Differential Sensitivity of Natural Killer Cells (NK) and Mononuclear Phagocytes (MP) to Leucylleucine-Methyl Ester (Leu-Leu-OMe)

Figure 6:
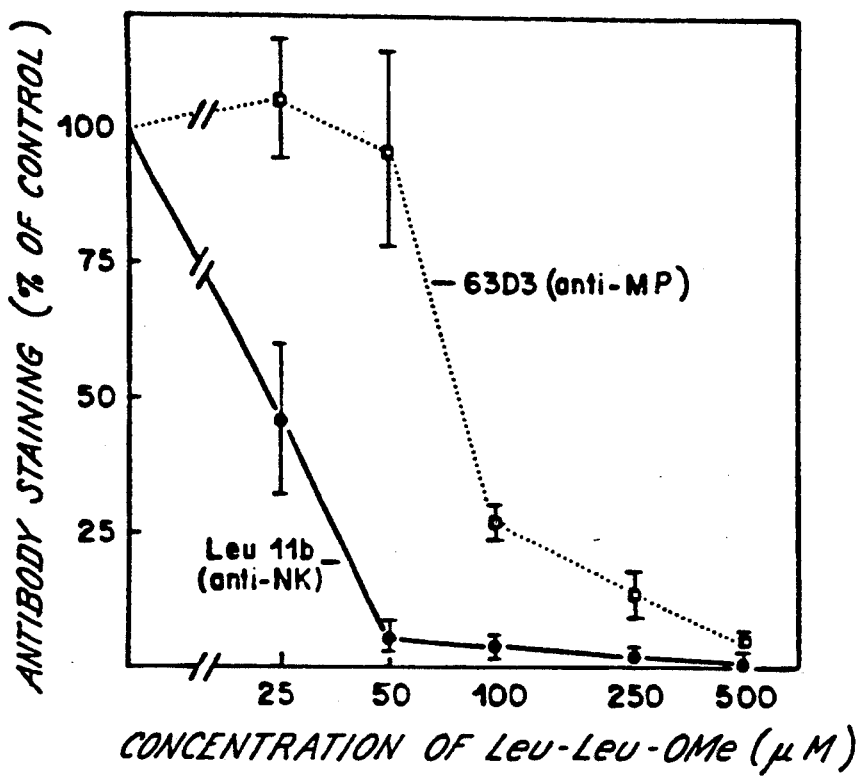
FIG. 6 shows the loss of NK and MP from PBM incubated with Leu-Leu-OMe at various concentrations.

In the experiments depicted in FIG. 6, freshly isolated PBM ($2.5 \times 10^6$/ml PBS and 1 g/l glucose) were incubated at room temperature with varying concentrations of Leu-Leu-OMe. After a 15 minute exposure to this compound, the cells were washed, incubated for 2 hours at 37° C. and then assessed for the percentage of remaining viable cells which were stained by anti-MP or anti-NK monoclonal antibodies. Preincubation with greater than 25–50 μM Leu-Leu-OMe led to loss of NK cells. This concentration of Leu-Leu-OMe did not deplete MP from PBM but higher concentrations of Leu-Leu-OMe caused loss of MP. The data is FIG. 6 show these results.

Anti-MP monoclonal antibodies (63D3) and anti-NK monoclonal antibodies (leu 11b) were obtained from Becton Dickinson Monoclonal Center, Inc., Mountain View, Calif. The antibody staining and Fluorescence Activated Cell Sorter (FACS) procedure was that of Rosenberg et al.[62] Data are expressed as percent of antibody staining in control cells (mean ±SEM, n=4).

EXAMPLE 11

Effects of O-Alkyl Esters Multiple Cell Types

The current example demonstrates that at concentrations 10 to 20 fold greater than those at which cytotoxic cells are ablated, Leu-Leu-OMe does have some minimal toxicity for certain non-cytotoxic lymphoid cells such as EBV transformed B cells and K562 cells. Yet, at present, the ability of Leu-Leu-OMe to function as a mediator of cell mediated cytotoxicity is the one unifying characteristic of the cell types which are rapidly killed by exposure to Leu-Leu-OMe.

Figure 7:
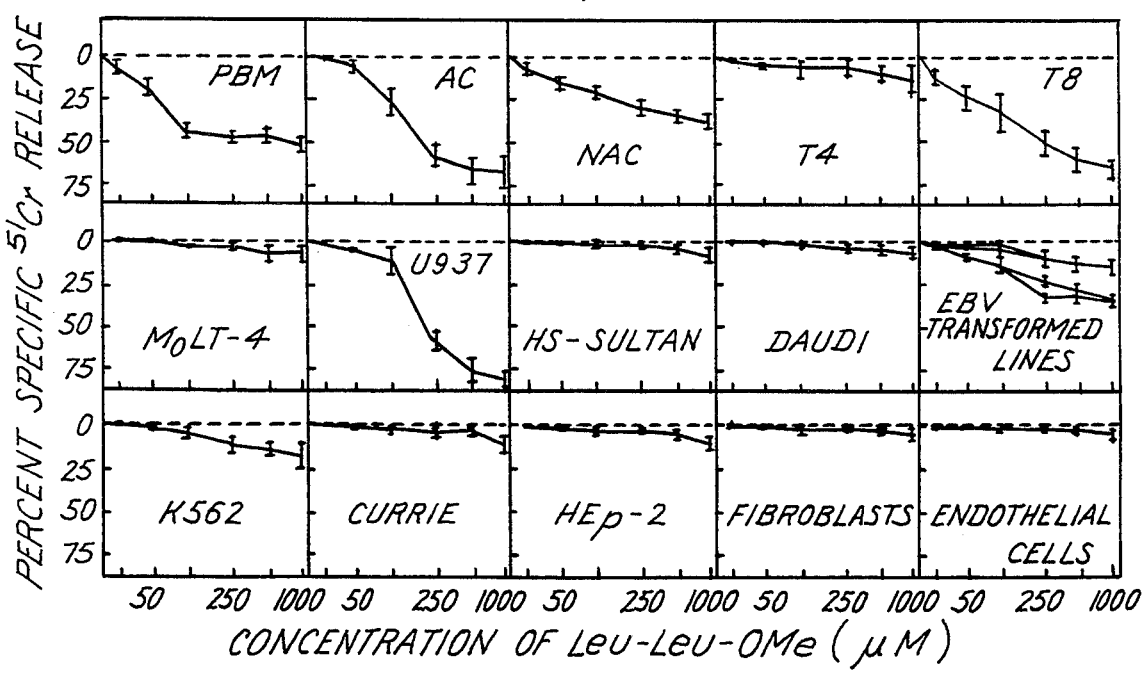
FIG. 7 shows the toxicity of various Leu-Leu-OMe concentrations for selected cell types.

In developing the data expressed in FIG. 7, cells ($2.5 \times 10^6$/ml) were exposed to the indicated concentrations of Leu-Leu-OMe for 15 minutes at room temperature, then specific $^{51}$Cr release during the next four hours was assessed. Data for the EBV transformed lines JM.6, SDL-G2, D8-219, and SM.4, respectively, are shown in order from top to bottom.

While it was clear that a substantial percentage of lymphocytes remained viable following exposure to even 1 mM Leu-Leu-OMe, the finding that disparate cell types such as MP and NK were both susceptible to Leu-Leu-OMe-mediated toxicity raised the possibility that this agent was a non-specific cell toxin. Therefore, the series of experiments depicted in FIG. 7 was performed to assess other cell types for evidence of toxicity following exposure to Leu-Leu-OMe.

To facilitate screening of multiple cell types for evidence of cell death following exposure to Leu-Leu-OMe, a $^{51}$Cr release assay was devised. In preliminary experiments it was noted that $^{51}$Cr release from MP-enriched populations exposed to varying concentrations of Leu-Leu-OMe correlated very closely with concentration-dependent loss of anti-MP antibody staining cells from PBM after similar incubation. Following brief exposures to Leu-Leu-OMe at room temperature, the loss of anti-MP antibody staining cells from PBM or the release of $^{51}$Cr from MP-enriched populations was always detectable within a 30 to 60 minute period of culture at 37° C. and maximal effects were seen within 3 to 4 hours.

Therefore, $^{51}$Cr release in a 4 hour assay was used in these experiments to assess toxicity from Leu-Leu-OMe. As shown in the first graph of FIG. 7, when the whole PBM population was exposed to varying concentrations of Leu-Leu-OMe, detectable $^{51}$Cr release was observed after exposure to 25 to 50 micromolar Leu-Leu-OMe, but only upon exposure to greater than 100 micromolar Leu-Leu-OMe was the maximal achievable $^{51}$Cr release from PBM observed. When MP-enriched adherent cells (AC) were similarly assessed, minimal $^{51}$Cr release was observed after exposure to 25–50 micromolar Leu-Leu-OMe whereas upon incubation with higher concentrations of this agent, more $^{51}$Cr release from AC was observed than with PBM.

When nylon wool non-adherent lymphocytes (NAC) were assessed, small but significant $^{51}$Cr release was observed with 25 to 50 micromolar Leu-Leu-OMe. When NAC were exposed to increasing concentrations of Leu-Leu-OMe, greater quantities of $^{51}$Cr release were observed. N-SRBC positive cells showed a dose-dependent Leu-Leu-OMe induced $^{51}$Cr release pattern indistinguishable from that of NAC. Since both antibody staining (FIG. 6) and functional studies (FIGS. 4A and 4B) have shown that 100 micromolar Leu-Leu-OMe causes maximal depletion of NK, this finding suggested that other lymphocytes were also susceptible to Leu-Leu-OMe toxicity at concentrations greater than 100 micromolar. When T4 enriched populations of T cells were assessed, however, it was clear that even 1000 micromolar Leu-Leu-OMe caused minimal $^{51}$Cr release from this population. In contrast, when N-SRBC positive cells were depleted of OKT4 positive cells, the remaining TS-enriched population produced high levels of $^{51}$Cr release following exposure to Leu-Leu-OMe.

When cell lines of myeloid or lymphoid origin were similarly assessed, selective toxicity of Leu-Leu-OMe was again observed. The human T cell leukemia line, MOLT-4, demonstrated no detectable Leu-Leu-OMe toxicity over a broad concentration range. The human plasma cell lines, HS-Sultan, and the B lymphoblastoid line, Daudi, demonstrated significant $^{51}$Cr release or alteration in subsequent proliferaive rate (data not shown) after exposure to a broad range of Leu-Leu-OMe concentrations. When the susceptibility of EBV-transformed B cell lines or clones to this agent was assessed, no significant toxicity of less than 250 micromolar Leu-Leu-OMe was seen. However, with higher concentrations of Leu-Leu-OMe, a variable degree of toxicity was seen.

Some EBV lines consistently displayed less than 20% $^{51}$Cr release even after exposure to 1 mM Leu-Leu-OMe, while other lines produced 25–35% $^{51}$Cr release after exposure to 250 micromolar Leu-Leu-OMe. In contrast, the human cell line U937 was susceptible to concentration-dependent Leu-Leu-OMe toxicity in a pattern indistinguishable from that of the peripheral blood MP with which this cell line shares many phenotypic and functional characteristics. After exposure to more than 250 micromolar Leu-Leu-OMe, extensive $^{51}$Cr release was observed and no viable proliferating U937 cell could be detected (data not shown). Similarly, the erythroleukemia line K562 demonstrated no significant $^{51}$Cr release or alteration in subsequent proliferative rate (date not shown) upon exposure to 100 micromolar or lower concentrations of Leu-Leu-OMe. With higher concentrations of Leu-Leu-OMe, modest amounts of $^{51}$Cr release and partial loss of proliferative capacity were observed (data not shown ).

In contrast, a variety of cell types of non-lymphoid, non-myeloid origin including human umbilical vein endothelial cells, the human renal cell carcinoma line, Currie, the human epidermal carcinoma line, HEp-2, and human dermal fibroblasts demonstrated no significant Leu-Leu-OMe induced $^{51}$Cr release. Furthermore, incubation of each of these non-lymphoid cell types with 500 micromolar Leu-Leu-OMe had no discernible effect on subsequent proliferative capacity (data not shown).

HS-Sultan, a human plasma cell line[63], Daudi, a B lymphoblastoid cell line[64], MOLT-4 an acute lymphoblastic T-cell leukemia line[65], and U-937, a human monocyte-like cell line[66] were obtained from the American Type Culture Collection, Rockville, Md. These lines as well as HEp-2 a human epidermoid carcinoma line; Currie, a human renal cell carcinoma line; and K562, a human erythroleukemia line were maintained in culture in medium RMPI supplemented with 10% FBS. Human dermal fibroblasts were serially passaged in culture as well while human umbilical vein endothelial cells were used after one subculture. Epstein Barr virus (EBV) transformed B lymphoblastoid cell lines JM.6 and SM.4 and cloned EBV transformed B cell lines SDL-G2 and D8-219 were maintained in culture in medium RPMI supplemented with 10% FBS.

In some experiments, toxicity of Leu-Leu-OMe for a variety of cell populations was assessed by $^{51}$Cr release. In assays where cells obtained from suspension culture were to be used, cells were labeled with Na$_2$$^{51}$CrO$_4$ (ICN, Plainview, N.Y.) for 60–90 minutes at 37° C. and then washed three times. Cells were then suspended in PBS (2.5×10$^6$/ml) and incubated in microtiter plates, 50 microL/well with indicated concentrations of Leu-Leu-OMe for 15 minutes at room temperature. In assays where cells were obtained from monolayer cultures, microtiter wells were seeded with cells (5×10$^4$/well) and cultured for 24 hours at 37° C. Cells were then labeled with Na$_2$$^{51}$CrO$_4$ while in adherent culture. Following $^{51}$Cr labeling, wells were thoroughly washed and varying concentrations of Leu-Leu-OMe added in 50 microL PBS and the plates incubated for 15 minutes at room temperature.

Following such initial serum-free incubations, 200 microL/well of medium RPMI containing 10% FBS were added and the plates incubated for another 4 hours prior to removal of 100 microliters of supernatant. Radioactivity in the supernatant was measured in an auto-gamma scintillation spectrometer (Packard Instrument Co., Downers Grove, Ill.). The percent specific release was calculated from the formula:

$$\% \text{ spec. release (rel)} = \frac{\text{exp. rel (cpm)} - \text{spont. rel (cpm)}}{\text{max. rel (cpm)} - \text{spont. rel (cpm)}}$$

in which maximal release refers to cpm obtained in wells containing 50% lysing agent (American Scientific Products, McGraw Park, Ill.) and spontaneous release refers to cpm released by cells incubated in control medium in the absence of Leu-Leu-OMe or the lysing agent. Only experiments in which spontaneous release was <25% (less than 25%) were used for subsequent data interpretation.

While the MP-like tumor line U937 was virtually identical to MP in susceptibility to Leu-Leu-OMe, none of the non-lymphoid, non-myeloid cell lines tested demonstrated such susceptibility to Leu-Leu-OMe-mediated toxicity.

EXAMPLE 12

Relative Sensitivity of CTL and NK to Leu-Leu-OMe

The present examples were designed to assess the relative sensitivity of NK and CTL to Leu-Leu-OMe. In the studies detailed in FIGS. 8A and 8B and 9, cytotoxicity assays were performed over a broad range of E:T ratios and units of lytic activity arising from equal numbers of responding lymphocytes were calculated and compared.

Figure 8A:
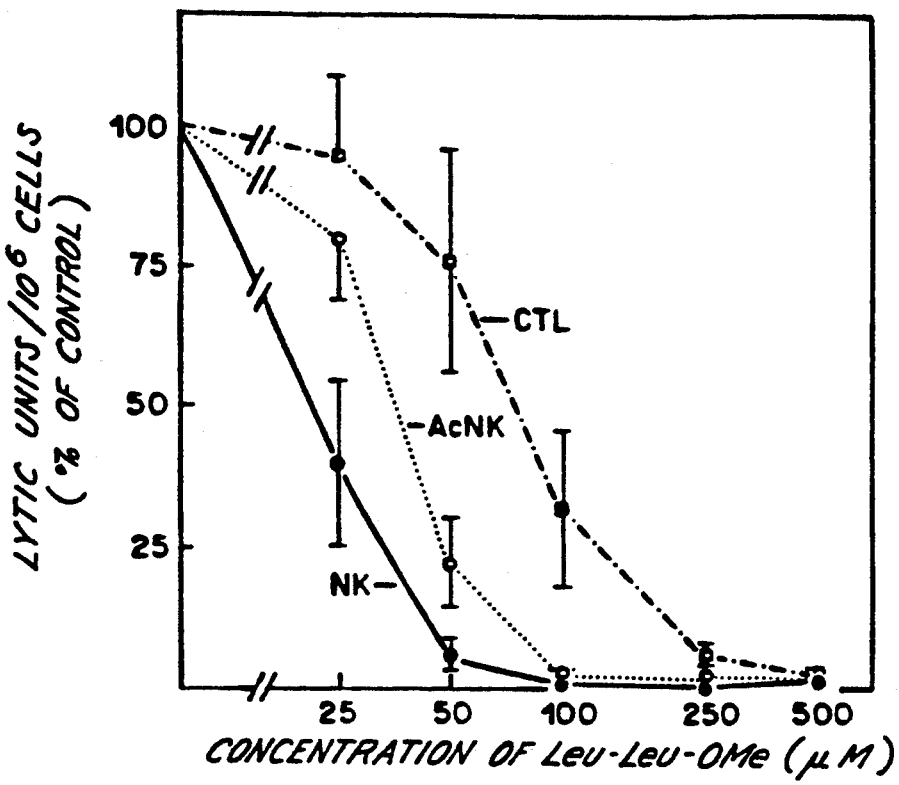
FIGS. 8A and 8B show the Leu-Leu-OMe mediated elimination of precursors of cytotoxic T lymphocytes activated NK ($A_c$NK) and NK.
Figure 8B:
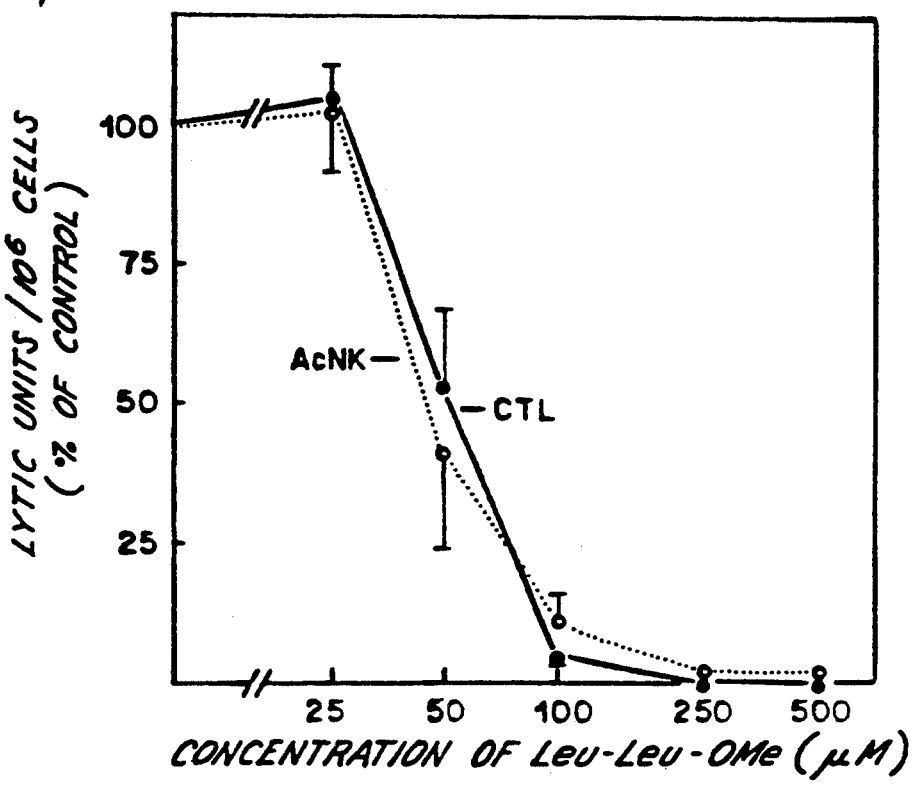

As shown in FIGS. 8A and 8B, both spontaneous NK and precursors of activated NK were totally eliminated by exposure to 100 $\mu$M (micromolar) Leu-Leu-OMe while CTL precursors, though diminished, were generally still present at greater than 50% of control levels. Only after exposure to greater than 250 $\mu$M (micromolar) Leu-Leu-OMe were all CTL precursors eliminated.

FIGS. 8A and 8B shows that incubation with Leu-Leu-OMe eliminates precursors of cytotoxic T lymphocytes (CTL) and activated NK-like cells (AcNK) Non-adherent lymphocytes ($2.5 \times 10^6$/ml) were incubated with the indicated concentrations of Leu-Leu-OMe for 15 minutes. Cells were then washed and either placed in mixed lymphocyte culture or assayed for specific lysis of K562 cells (NK). After 6 day MLC, cells were assayed for specific lysis of allogeneic stimulator lymphoblasts (CTL) or K562 (AcNK). Data are expressed as percent of control lytic units (mean+SEM, n=6).

Figure 9:
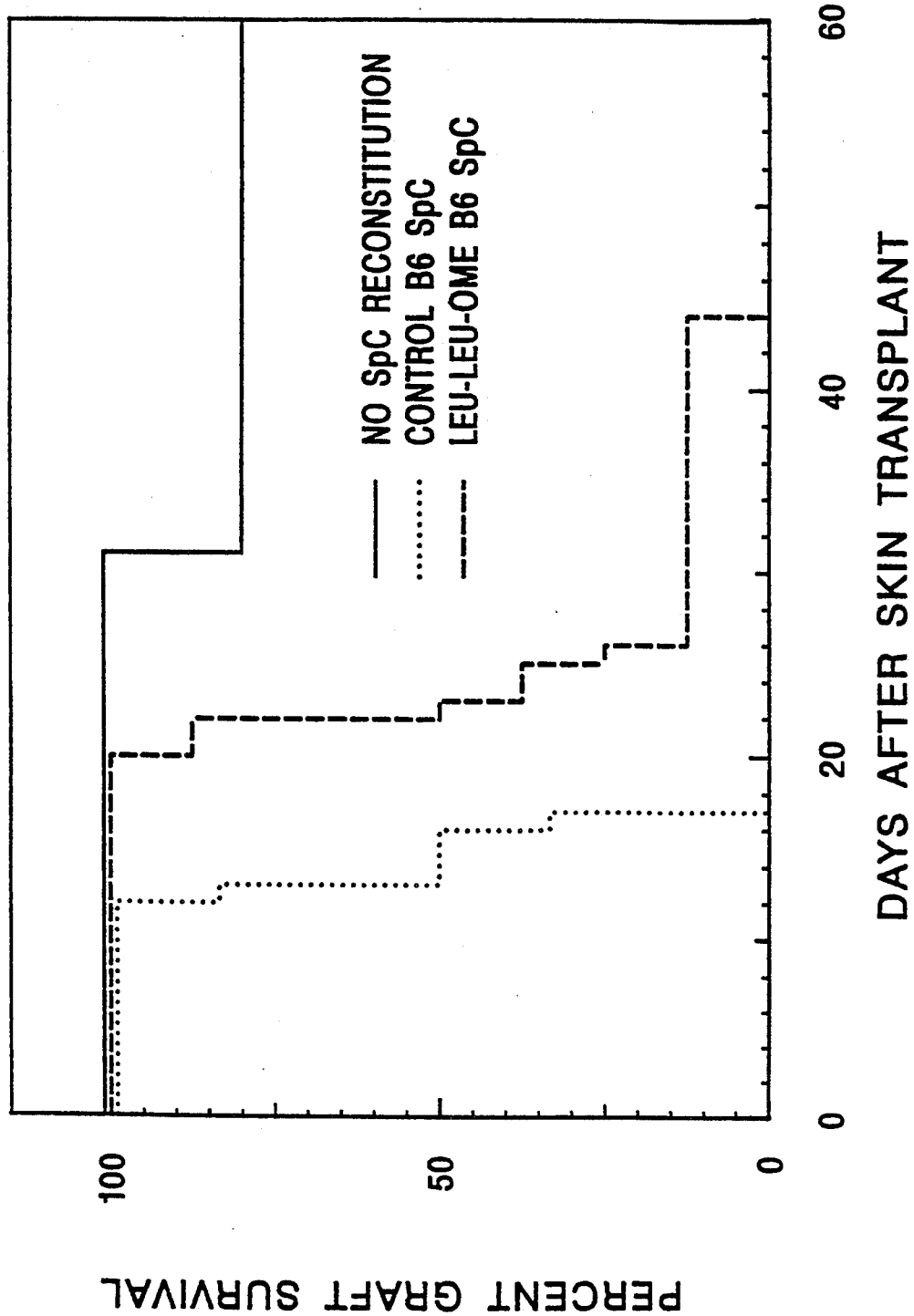
FIG. 9 shows the survival of B6D2F1 skin grafts applied to ATXBM, TCD mice in the presence or absence of reconstitution with control or Leu-Leu-OMe treated B6 SpC. Four weeks after treatment of ATXBM mice with anti-L3T4 and anti-Lyt 2, mice were infused with $70 \times 10^6$ control B6 SpC ( . . . , 6 mice), $70 \times 10^6$ Leu-Leu-OMe treated B6 SpC ( - - , 8 mice), or no SpC ( - - - , 5 mice). B6D2F1 skin grafts were applied within 24 hours. Results are expressed as the time interval between time of skin graft application and complete necrosis of the graft.

When the elimination of CTL and activated NK precursors by Leu-Leu-OMe was compared to that of spontaneous NK, the mean Leu-Leu-OMe concentration required to diminish lytic activity by 75% was significantly greater for elimination of CTL precursors ($123 \pm 25$ $\mu$M than for elimination of precursors of activated NK ($50 \pm 5$ $\mu$M, p>0.05). Both values were also higher than the mean concentration of Leu-Leu-OMe required to diminish spontaneous NK lytic activity by 75% (35 $\mu$M $\pm 4$ $\mu$M. FIG. 9 shows that, following activation, CTL and AcNK became identical in sensitivity to Leu-Leu-OMe. After 6 day MLC, cells were incubated for 15 minutes with the indicated concentrations of Leu-Leu-OMe, then assayed for CTL or AcNK activity as for FIGS. 8A and 8B. Thus, only after MLC activation did CTL display a sensitivity to Leu-Leu-OMe toxicity that was equal to that of NK cells.

EXAMPLE 13

Ex vivo Dipeptide Alkyl Ester Treatment in Graft vs Host Disease and Graft Rejection The present example is provided to demonstrate the role of dipeptide alkyl ester, particularly O-alkyl ester (e.g., Leu-Leu-OMe)-sensitive CTL in graft rejection in vivo. The particular in vivo model employed in the present study was the $C_{57}BL/6J$ (B6) mouse model. This particular animal model is also used to demonstrate the use of the referenced dipeptide alkyl esters and O-alkyl esters in diminishing and/or preventing lethal graft vs host disease and graft rejection, most particularly, acute allograft rejection. The data presented herein employing the particularly defined dipeptide alkyl esters and O-alkyl dipeptide esters demonstrate that T-cell mediated cytotoxicity plays a major, if not essential, role in mediating skin graft or other forms of organ allograft rejection in vivo.

The experimental design employed in the present study examines whether removal of Leu-Leu-OMe-sensitive, DPPI-enriched CTL is effective in preventing or modulating rejection of Class I+II MHC and multiple non-MHC dispartate skin allografts. Leu-Leu-OMe-treated C57BL6/J (B6) SpC (h-$2^b$) are demonstrated herein to be unable to generate lethal GVHD in euthymic or thymectimized B6D2F1 (h-$2^{b,d}$) recipient mice. Moreover, while transfer of Leu-Leu-OMe-treated B6 SpC to rigorously T cell depleted, thymectomized B6 host mice was sufficient to allow rejection of B6D2F1 skin grafts, the rate of skin graft rejection in these animals was significantly delayed. Thus, the data presented herein indicates that Leu-Leu-OMe sensitive CTL appear to play an active role in acute skin graft rejection.

As the host thymus has been shown to play a major role in the establishment of tolerance to both donor and host alloantigens following bone marrow transplantation, the role of the thymus on the course of GVHD was also examined.

Materials and Methods

Mice. C57BL/6J (B6) and (C57BL/6xDBA/2)F1 female mice were purchased from the Jackson Laboratory, Bar Harbor, Me.

Medium. RPMI 1640 (Hazleton Research Products, Denver, Pa.) supplemented with 5 mM HEPES, 1 mM sodium pyruvate, $10^{-4}$ M 2-mercaptoethanol, penicillin G (200 U/ml), (gentamicin (10 $\mu$g/ml), L-glutamine (0.3 mg/ml) and 10% fetal bovine serum was used for cell cultures.

Antibodies. For in vivo cell depletion, anti-L3T4 (GK1.5, 16) and anti-Lyt2 (YTS 169.4, 17) were purified from hybridoma culture supernatant by ammonium sulfate precipitation and binding to staphylococcal protein A-columns. The IgG fraction of rabbit anti-mouse thymocyte globulin was purchased from Accurate Chemical and Scientific Corporation, San Diego, Calif. For in vitro depletion of T cells, anti-Thyl.2 (HO-13-4, 18), anti-L3T4 (2B6, 19) anti-L3T4 (2B6, 19) and anti-Lyt 2 (3.155, 20) were prepared as culture supernatants of hybridoma cells obtained from the American Type Culture Collection, Rockville.

Cell preparation. Bone marrow cells (BMC) were flushed from femurs and tibias, were suspended in Hanks' balanced salt solution (HBSS), and were filtered through sterile nylon mesh. Spleen cells (SpC) were suspended in HBSS, filtered through sterile nylon mesh and then washed. For depletion of T cells, suspensions of cells ($40 \times 10^6$/ml) were incubated for 30 min. at 4° C. with anti-Thyl.2, anti-L3T4 (2B6) and anti-Lyt 2 (3.155) and then rabbit complement (1:8, Pel Freez, Rogers, Ark.), previously adsorbed with mouse spleen cells, was added, and cells were incubated at 37° C. for an additional 50 minutes. Cells were then pelleted by centrifugation and resuspended in fresh medium an dfresh complement and incubated at 37° C. for an additional 50 minutes. Cells were then washed two times in HBSS.

Incubation with Leu-Leu-OMe. Leu-Leu-OMe was synthesized from leucyl-leucine (Sigma) as described by Thiele et al. (1985).[61]Cells were washed and suspended (2.5 to $10\times10^6$/ml) in PBS and were incubated for 15 min. at room temperature with 250 μM Leu-Leu-OMe. Cells were then washed, resuspended in culture medium, and placed in culture or infused in vivo within 1 hour.

Cell identification procedures. For identification of B cells, SpC were stained with fluorescein conjugated F(ab')$_2$ goat anti-mouse immunoglobulin (Fl-GAMIg, Cooper Biomedical, Malvern, Pa). Thy.2(+) cells were identified by incubation with HO-13-4 culture supernatant followed by staining with Fl-GAMIg and the number of Thy1.2 (+) cells determined by subtraction of the number of cells directly staining with Fl.GAMIg from these staining with Fl.GAMIg after initial incubation with anti-Thy1.2 (HO-13-4). L3T4(+) or Lyt2(+) cells were identified by incubation with GK1.5 or YTS 169.4 followed by staining with fluorescein conjugated F(ab')$_2$ mouse anti-rat IgG (Jackson Immunoresearch, West Grove, Pa.), a secondary antibody with very low levels of direct staining (<1%) of mouse SpC. Cells were analyzed on a Becton Dickinson FACStar flow cytometer as described by Thiele et al. (1986).[67] Bone marrow transplantation. Recipients were maintained on acidified (ph 2), antibiotic (neomycin, 100 mg/liter, and polymyxin B, 10 mg/liter) H$_2$O for 2 to 3 days before and 7 days after transplantation. On the day of transplantation, recipients were irradiated (900 cGy) and 2 to 6 h later were injected via the lateral tail vein with donor cells in 0.5 ml of HBSS.

Preparation of adult thymectomized bone marrow reconstituted (ATXBM), T cell depleted (TCD) mice. Adult thymectomy of B6 mice was performed at 5-6 weeks of age by the method of Miller.[68] Mice were allowed to recover for at least ten days before irradiation (900 cGy) and transplantation with $5\times10^6$ anti-Thy1.2, anti-L3T4 (2B6) and anti-Lyt2 (3.155)+C' treated B6 BMC. In addition, all mice were injected intraperitoneally with 200 μg/d of anti-L3T4 (GK1.5) and 100 μg/d anti-Lyt2 (YTS169.4) for three consecutive days. These does of anti-T cell antibodies were 2-fold greater than those at which >95% depletion of L3T4(+) and Lyt2(+) splenic T cells was observed 3 days after completion of this regimen in euthymic, control B6D2F1 mice. In some experiments, on the second day of anti-L3T4 and anti-Lyt2 treatment, mice were also injected intraperitoneally with 0.5 mg of rabbit anti-thymocyte globulin, a dose 2-fold in excess of that observed to cause >90% depletion of L3T4(+) and Lyt2(+) T cells from euthymic control mice.

Skin grafting. Three to four weeks after completion of in vivo anti-T cell therapy, ATXBM, TCD mice wre reconstituted wth $70\times10^6$ control B6 SpC, $70\times10^6$ Leu-Leu-OMe treated B6 SpC or no SpC, Within 24 hours, B6D2F1 tail skin in pieces aproximately 4 mm $\times$ 10 mm was grafted onto the lateral thoracic wall of recipient mice. The general technique of free skin grafting described by Billingham et al. (1951)[69] was adapted for use in the grafting of skin grafts to the mouse model of the present example, which reference is specifically incorporated herein by reference for this purpose. The grafts were covered with vaseline impregnated gauze and plaster bandages which were removed 8-10 days after grafting. The grafts were observed daily for rejection, which was considered complete when no viable skin was visible.

The immunomodulatory effects of Leu-Leu-OMe treatment of effector T cells is demonstrated to alter the course of solid organ graft rejection. In the present study, effector T cells were treated ex vivo with the described dipeptide alkyl esters. B6 female mice (5-6 weeks of age) were serially thymectomized, lethally irradiated, reconstituted with T cell depleted B6 BMC and infused with anti-CD4 and anti-CD8 mAb's as described supra. Two months after completion of this regimen, SpC from such ATXBM, TCD mice were analyzed by flow cytometry for the presence of residual T cells. As indicated by the results detailed in Table 4, the spleens of these animals contained less than or equal to 1% CD4(+) or CD8(+) T cells. Long-term reconstitution with CD4(+) and with CD8(+) T cells was achieved when such ATXBM, TCD B6 mice were infused with $70\times10^6$ control or Leu-Leu-OMe treated B6 SpC. (See Table 4)

When B6D2F1 skin grafts were applied to unreconstituted ATXBM, TCD mice, long-term skin graft survival was seen in four of five mice (see FIG. 9). In the single animal in this group in which skin graft rejection was observed, subsequent fluorescence activated cell disorder (FACs) analysis revealed the presence of 12% CD4(+) and 3% CD8(+) cells within the spleen, suggesting that this animal represented a sporadic failure of the thymectomy and/or T cell depletion regimen, as all other animals in this experimental group were found to have less than 1% CD4(+) or CD8(+) T cells. When $70\times10^6$ control B6 SpC were infused into ATXBM, TCD mice, brisk rejection of B6D2F1 skin grafts by all animals was observed (FIG. 9). When B6 SpC treated with 250 μM Leu-Leu-OMe were infused into ATXBM, TCD mice, rejection of B6D2F1 skin by all mice was again observed. The duration of skin graft survival, however, was significantly prolonged in the recipients of Leu-Leu-OMe treated donor cells relative to that observed in recipients of control cells (p <0.001 by Mann-Whitney non-parametric analysis).

Applicants postulate that either a CTL depleted, Leu-Leu-OMe treated B6 SpC alone are capable of mediating rejection of B6D2F1 skin grafts, or that Leu-Leu-OMe resistant B6 SpC were providing T helper cell function necessary to generate cytotoxic effector cells from residual T cells or other cells present within ATXBM, TCD mice. In particular, as only irradiation and anti-CD4 and anti-CD8 mAb were employed to deplete T cells from the thymectomized host animals used in this example, Applicants postulate that radio resistant CD4-, CD8- host CTL might be serving as effector cells in skin graft rejection observed in these experiments. Therefore, additional experiments were carried out in which an injection of rabbit anti-mouse thymocyte globulin was added to the host T cell depletion regimen. Hemisplenectomies were performed in all animals as a control to verify efficacy of thymectomy and T cell depletion. Only animals without detectable CD4(+) or CD8(+) T cells were used in subsequent skin graft experiments. As shown in the results detailed in Table 5, uniform, albeit delayed, rejection of B6D2F1 skin grafts was again observed following transfer of Leu-Leu-OMe treated B6 SpC to such ATXBM pan-T cell depleted hosts.

TABLE 4

LONG TERM CELL RECONSTITUTION OF ATXBM, TCD MICE FOLLOWING TRANSFER OF CONTROL OR LEU—LEU—OME TREATED SPC

| Mice | SpC Reconstitution | Mean Staining of SpC[a] | | | |
|------|---------------------|-----|------|------|------|
|      |                     | sIG | Thy1 | L3T4 | Lyt2 |
| ATXBM, | Nil | 74 ± 4 | 15 ± 3 | <1 | <1 |

TABLE 4-continued

LONG TERM CELL RECONSTITUTION OF ATXBM, TCD MICE FOLLOWING TRANSFER OF CONTROL OR LEU—LEU—OME TREATED SPC

| Mice | SpC Reconstitution | Mean Staining of SpC$^a$ | | | |
|---|---|---|---|---|---|
| | | sIG | Thy1 | L3T4 | Lyt2 |
| TCD | | | | | |
| | Control SpC | 68 ± 4 | 23 ± 4 | 10 ± 2 | 6 ± 3 |
| | Leu—Leu—OMe Treated SpC | 69 ± 3 | 18 ± 5 | 14 ± 3 | 4 ± 1 |
| Control B6 | Nil | 53 ± 4 | 42 ± 3 | 19 ± 3 | 18 ± 4 |

$^b$Results represent means of values obtained in 3 animals within each experimental group. Thymectomized, T cell depleted mice were sacrificed 100 days after infusion of 70 × 10$^6$ control B6 SpC, 70 × 10$^6$ Leu—Leu—OMe treated B6 SpC or cell free medium.

TABLE 5

ALLOGENEIC SKIN GRAFT REJECTION IS SEEN FOLLOWING TRANSFER OF LEU—LEU—OME TREATED SPC TO ATXBM MICE TREATED WITH ANTI-L3T4, ANTI-LYT2 AND ANTI-THYMOCYTE GLOBULIN

| Spleen Cell Reconstitution | Number of Mice Per Group | B6D2F1 Skin Graft Survival (Days) |
|---|---|---|
| Nil | 2 | >45d$^b$, >60d |
| Control B6 SpC | 3 | 12d, 13d, 17d |
| Leu—Leu—Ome Treated B6 SpC | 2 | 20d, 23d |

$^a$B6 host mice were thymectomizd, irradiated (900 cGy) and reconstituted with T cell depleted B6 BMC as detailed in Figure 1. Three weeks after BMC reconstitution, mice were injected intraperitoneally on three consecutive days with 200 μg of anti-L3T4 (GK 1.5) and 100 μg of anti-Lyt2 (YTS 169.4) and on the second day of anti-L3T4 and anti-Lyt 2 treatment with 0.5 mg of rabbit anti-mouse thymocyte globulin.
$^b$Mouse died with intact skin graft 45 days after skin graft applied.

Figure 10B:
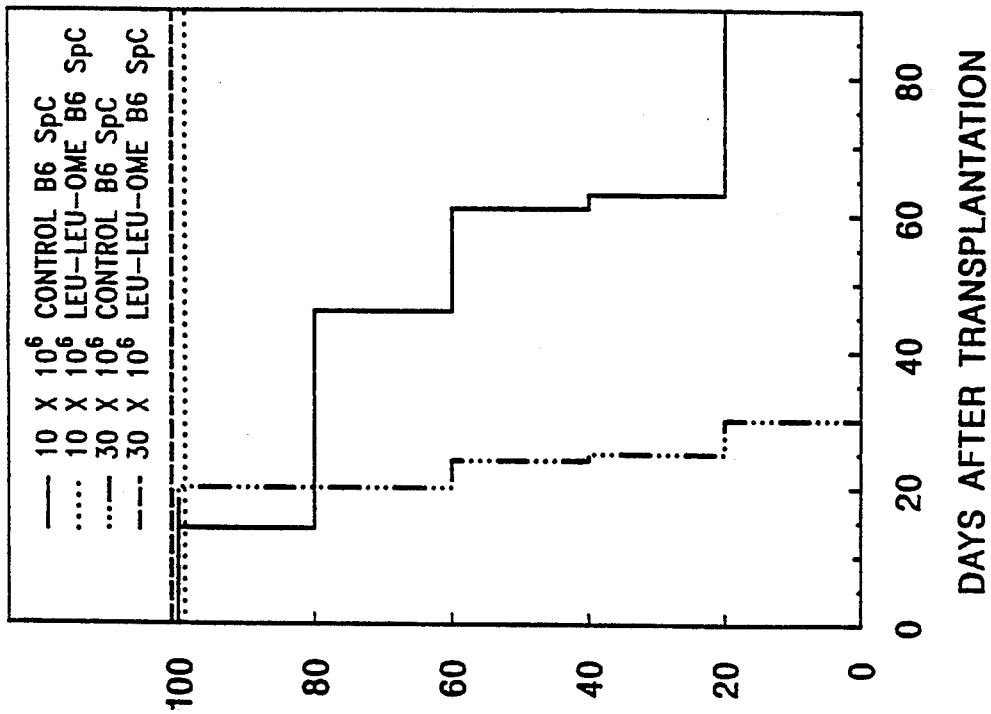
FIGS. 10A and 10B show Leu-Leu-OMe treatment of B6 donor SpC prevents lethal GVHD in euthymic or thymectomized B6D2F1 recipients. After irradiation, all recipient mice received $5 \times 10^6$ anti-Thy1.2+C' and Leu-Leu-OMe treated BMC and the indicated numbers of control or Leu-Leu-OMe treated B6 SpC. All survival curves represent groups of 5 animals except that data are shown for ten thymectomized recipients of $10 \times 10^6$ Leu-Leu-OMe treated B6 SpC.
Figure 10A:
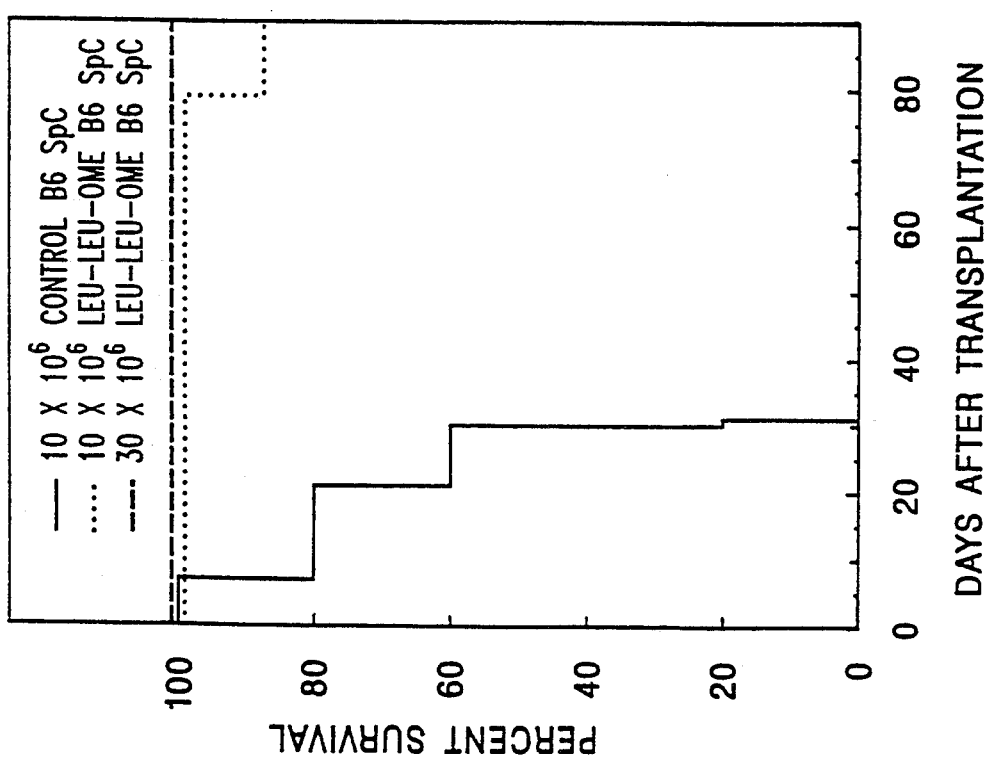

These results indicate that Leu-Leu-OMe resistant B6 T cells are capable of mediating delayed B6d2F1 skin graft rejection. Transfer of 10×10$^6$ control B6 SpC into thymectomized B6D2f1 mice (FIG. 10A) induced more rapid lethal GVHD than noted in euthymic B6D2F1 recipients of the same number of B6 donor cells (FIG. 10B). Despite the enhanced vulnerability of thymectomized B6D2F1 mice to GVHD, Leu-Leu-OMe treatment of donor B6 SpC prevented lethal GVHD as effectively as was noted with control recipients.

The present example demonstrates a method of inhibiting graft rejection through the administration of particular alkyl esters of dipeptides, most particularly through administration of an O-alkyl ester. The most preferred O-alkyl dipeptide ester is L-leucyl-L-leucinememethyl ester (Leu-Leu-OMe). The present methods may be used in conjunction with any type of tissue graft to inhibit tissue or whole organ rejection. In such an application, the prospective transplant recipient is first identified and then prospective transplant recipient is then treated with an effective amount of an alkyl ester of a dipeptide consisting of natural or synthetic L-amino acids with hydrophobic side chains.

The present methods, however, are most preferably employed in conjunction with skin grafts. Thus, the present disclosure provides a method whereby the rejection of skin and potentially other tissue grafts may be prevented in an animal, for example, of skin grafts in mouse and in human graft recipients.

Changes may be made in the construction, operation and arrangement of the various elements, steps and procedures described herein without departing from the concept and scope of the invention as defined in the following claims.

BIBLIOGRAPHY

The following references are cited throughout the body of the present Application. These references are specifically incorporated herein by reference for the purposes indicated throughout the Specification.

1. Thiele et al. (1983) *J. Immunol.* 131:2282-2290.
2. Goldman et al. (1973) *J. Biol. Chem.*, 254:8914.
3. Goldman et al. (1973) *FEBS (Fed. Europ. Biol. Sci.) Letters*, 33: 208-217.
4. Reeves (1979) *J. Biol. Chem.*, 254:8914-8921.
5. Reeves et al. (1981) *Proc. Nat'l. Acad. Sci.*, 78:4426-4429.
6. Gidlund et al., (1978) *Nature*, 223:259
7. Dempsey et al. (1982) *J. Immunol.*, 129:1314.
8. Domzig et al. (1983) *J. Immunol.*, 130:1970.
9. Quan et al. (1982) *J. Immunol.*, 128:1786.
10. Hiserodt et al. (1982) *J. Immunol.*, 129:1782,2266.
11. Verhoef et al. (1983) *J. Immunol.*, 131:125.
12. Roder et al. (1979) *J. Immunol.*, 123:2785.
13. Kendall et al. (1980) *J. Immunol.*, 125:2770.
14. Katz (1982) *J. Immunol.*, 129:287.
15. Hattori et al. (1983) *J. Immunol.*, 131:662.
16. Seaman (1983) *J. Immunol.*, 131:2953.
17. Koren et al. (1982) *Mol. Immunol.*, 19:1341.
18. Seaman et al. (1982) *J. Clin. Invest.*, 69:876.
19. Timonen et al. (1981) *J. Exp Med.*, 153:569-582.
20. Seeley et al. (1979) *J. Immunol.*, 123:1303.
21. Grimm et al. (1982) *J. Exp. Med.*, 155:1823.
22. Kleinermann et al. (1984) *J. Immunol.*, 133:4.
23. Ortaldo et al. (1981) *J. Immunol.*, 127:2401.
24. Perussia et al. (1983) *J. Immunol.*, 130:2133.
25. Zarling et al. (1981) *J. Immunol.*, 127:2575.
26. Nieminen et al. (1984) *J. Immunol.*, 133:202.
27. Calvo et al. (1984) *J. Immunol.*, 132:2345.
28. Breard et al. (1980) *J. Immunol.*, 124:1943.
29. Gidlund et al. (1978) *Nature*, 223:259.
30. Trinchieri et al. (1978) *J. Exp. Med.*, 147: 1314.
31. Bonavida et al. (1983) *Immunol. Rev.*, 72:119.
32. Podack et al. (1983) *Nature*, 302: 442.
33. Dennert et al. (1983) *J. Exp. Med.*, 157:1483.
34. Burns et al. (1983) *Proc. Nat'l. Acad. Scio*, 80:7606.
35. Wells et al., *In:Basic and Clinical Immunology*, Fundenbergo et al. (editors) 2nd ed. Lange (1978) P493.
36. Dokhelar et al. (1981) *Transplantation*, 31:61.
37. Lopez et al. (1979) *Lancet*, 2:1103.
38. Lopez et al. (1980) *Lancet*, 2:1025.
39. Sullivan et al. (1981) *Blood*, 57:207.
40. Lopez et al. (1980) *Lancet*, 2:1025
41. Korngold et al. (1978) *Exp. Med.*, 148:1687.
42. Reisner et al. (1983) *Blood*, 61:341.
43. Cudkowicz et al. (1971) *J. Exp. Med.*, 134:83.
44. Kiessling et al. (1977) *Eur. J. Immunol.*, 7:655.
45. Warren et al. (1977) *Nature*, 300:655.
46. Herberman et al. (1981) *Science*, 214: 24.
47. Mayer et al. (1985) *J. Immunol.*, 134:258.
48. Fennel (1981) *Pathol. Annu.*, 16:289.
49. Komiyama et al. (1982) *Blood*, 60:1428.
50. Itoh et al. (1983) *Blood*, 61:940.
51. Komiyama et al. (1984) *Cancer*, 54: 1547.
52. Hansson et al. (1981) *Eur. J. Immunol.*, 11:8.
53. Hansson et al. (1982) *J. Immunol.*, 129:126.
54. Spitzer et al. (1984) *Blood*, 63: 620.
55. Torok-Storb et al. (1982) *Nature*, 298: 473.
56. Mangan et al. (1984) *Blood*, 63:260.
57. Mangan et al. (1982) *J. Clin. Invest.*, 70:1148.
58. Nogasawa et al. (1981) *Blood*, 57:1025.

59. Holmberg et al. (1984) *J. Immunol.*, 133:2933.
60. Rosenberg et al. (1975) *J. Immunol.*, 122:831–926.
61. Thiele et al. (1985) *J. Immunol.*, 134:786–793.
62. Rosenberg et al. (1981) *J. Immunol.*, 126:1473.
63. Goldblum et al. (1973) *In:Proc. Seventh Leucocyte Cultural Conference;* ed, Da Guilland, Acad. Press N.Y. pp 15–28.
64. Klein et al. (1968) *Cancer Res.*, 28:1300.
65. Monowada et al. (1972) *J. Nat'l. Canc. Inst.*, 49:891.
66. Koren et al. (1979) *Nature,* 279:891.
67. Thiele et al. (1986) *J. Immunol,* 136:1038
68. Miller, JFAP (1960) *Bc. J. Cancer,* 14:93.
69. Billingham et al. (1951), *J. Exp. Med.*, 28:385.
70. Murphy et al. (1987), *J. Exp. Med.,* 166: 1499–1509.
71. Burges et al. (1981), *Eur. J. Immunol.*, 11:657–661.
72. Herold et al. (1986), *J. Immunol.*, 136: 1315–1321.

What is claimed is:

1. A method of treating a tumor of myeloid or lymphoid origin which is sensitive to dipeptide alkyl esters comprising administering a therapeutically effective amount of an alkyl ester of a dipeptide consisting essentially of the L-amino acid leucine, said alkyl dipeptide ester being sufficient to substantially deactivate natural killer cells or cytotoxic T-lymphocytes.

2. A method of treating a patient having a tumor of myeloid or lymphoid origin which is sensitive to dipeptide alkyl esters comprising administering a therapeutically effective amount of an alkyl ester of a dipeptide consisting essentially of natural or synthetic L-leucine with hydrophobic side chains, said alkyl dipeptide ester being sufficient to substantially deactivate natural killer cells or cytotoxic T-lymphocytes.

3. The method of claim 1 or 2 wherein the therapeutically effective amount is between about $1 \times 10^{-4}$ moles per kg and $1 \times 10^{-2}$ moles per kg weight of the patient.

4. The method of claim 1 or 2 wherein the alkyl ester is a methyl ester, an ethyl ester, a propyl ester, an isopropyl ester, a butyl ester or an isobutyl ester.

* * * * *